(12) United States Patent
Shelton, IV et al.

(10) Patent No.: US 10,842,496 B2
(45) Date of Patent: Nov. 24, 2020

(54) IMPLANTABLE SPHINCTER ASSISTANCE DEVICE WITH TUNED MAGNETIC FEATURES

(71) Applicant: ETHICON LLC, Guaynabo, PR (US)

(72) Inventors: Frederick E. Shelton, IV, Hillsboro, OH (US); Michael D. Cronin, Cincinnati, OH (US); Kevin M. Fiebig, Cincinnati, OH (US); Andrew R. Conway, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 109 days.

(21) Appl. No.: 16/222,195

(22) Filed: Dec. 17, 2018

(65) Prior Publication Data

US 2020/0187949 A1 Jun. 18, 2020

(51) Int. Cl.
  *A61B 17/12* (2006.01)
  *A61F 2/04* (2013.01)
  *A61B 17/00* (2006.01)

(52) U.S. Cl.
  CPC .......... *A61B 17/12013* (2013.01); *A61F 2/04* (2013.01); *A61B 2017/00876* (2013.01); *A61F 2002/044* (2013.01); *A61F 2210/009* (2013.01); *A61F 2230/0065* (2013.01); *A61F 2250/0009* (2013.01)

(58) Field of Classification Search
  CPC ........ A61B 17/12009; A61B 17/12013; A61B 2017/12018; A61F 2002/045; A61F 2002/044

See application file for complete search history.

(56) References Cited

U.S. PATENT DOCUMENTS

| 5,122,136 A | 6/1992 | Guglielmi et al. |
| 5,204,382 A | 4/1993 | Wallace et al. |
| 5,509,888 A | 4/1996 | Miller |

(Continued)

FOREIGN PATENT DOCUMENTS

| DE | 3011742 A1 | 10/1981 |
| EP | 1547549 A2 | 6/2005 |

(Continued)

OTHER PUBLICATIONS

U.S. Appl. No. 15/908,875, entitled Laparoscopic Sizing Instrument, filed Mar. 3, 2018.

(Continued)

*Primary Examiner* — Wade Miles
(74) *Attorney, Agent, or Firm* — Frost Brown Todd LLC

(57) ABSTRACT

An implantable restriction device includes a plurality of beads and a plurality of links that join the beads together. The beads include a housing including a contact surface, a passageway extending through the hosing along an axis, and at least one magnet disposed around the passageway. Portions of the links are slidably disposed in corresponding passageways of the beads such that the beads are operable to transition between a constricted configuration and an expanded configuration. The contact surfaces of adjacent beads abut against each other in the constricted configuration. Adjacent magnets within adjacent beads generate an interactive magnetic field foxed on the abutting contact surfaces of adjacent beads.

14 Claims, 22 Drawing Sheets

(56) References Cited

U.S. PATENT DOCUMENTS

| | | |
|---|---|---|
| 5,702,361 A | 12/1997 | Evans, II et al. |
| 6,543,456 B1 | 4/2003 | Freeman |
| 7,175,589 B2 | 2/2007 | Deem et al. |
| 7,374,565 B2 | 5/2008 | Hassler, Jr. et al. |
| 7,390,294 B2 | 6/2008 | Hassler, Jr. |
| 7,445,010 B2 | 11/2008 | Kugler et al. |
| 7,481,763 B2 | 1/2009 | Hassler, Jr. et al. |
| 7,695,427 B2 | 4/2010 | Kugler et al. |
| 7,727,141 B2 | 6/2010 | Hassler, Jr. et al. |
| 7,879,068 B2 | 2/2011 | Dlugos et al. |
| 8,070,670 B2 | 12/2011 | Deem et al. |
| 8,603,023 B2 | 12/2013 | Albrecht et al. |
| 8,617,049 B2 | 12/2013 | Dlugos, Jr. et al. |
| 8,636,751 B2 | 1/2014 | Albrecht et al. |
| 8,715,157 B2 | 5/2014 | Berg et al. |
| 8,734,475 B2 | 5/2014 | Ekvall et al. |
| 8,870,742 B2 | 10/2014 | Dlugos, Jr. et al. |
| 8,876,761 B2 | 11/2014 | Albrecht et al. |
| 10,405,865 B2 | 9/2019 | Shelton, IV et al. |
| 2005/0283235 A1 | 12/2005 | Kugler et al. |
| 2009/0062824 A1 | 3/2009 | Berg et al. |
| 2011/0098731 A1 | 4/2011 | Whitbrook et al. |
| 2014/0336696 A1 | 11/2014 | Kugler et al. |
| 2017/0055986 A1 | 3/2017 | Harris et al. |
| 2018/0325643 A1* | 11/2018 | Kappus ................ A61F 2/0036 |
| 2019/0029688 A1* | 1/2019 | Shelton, IV .............. A61F 2/04 |
| 2019/0029689 A1* | 1/2019 | Shelton, IV ..... A61B 17/12009 |
| 2019/0274803 A1* | 9/2019 | Auld ................ A61B 17/12009 |
| 2020/0187949 A1* | 6/2020 | Shelton, IV .............. A61F 2/04 |
| 2020/0188080 A1* | 6/2020 | Fiebig ............. A61B 17/12099 |
| 2020/0188081 A1* | 6/2020 | Shelton, IV .......... A61F 2/0004 |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |

OTHER PUBLICATIONS

U.S. Appl. No. 15/914,381, entitled "Tunable Magnetic Sphincter Augmentation Device," filed Mar. 7, 2018.

U.S. Appl. No. 15/914,407, entitled "MRI Compatible Magnetic Sphincter Augmentation Device," filed Mar. 7, 2018.

* cited by examiner

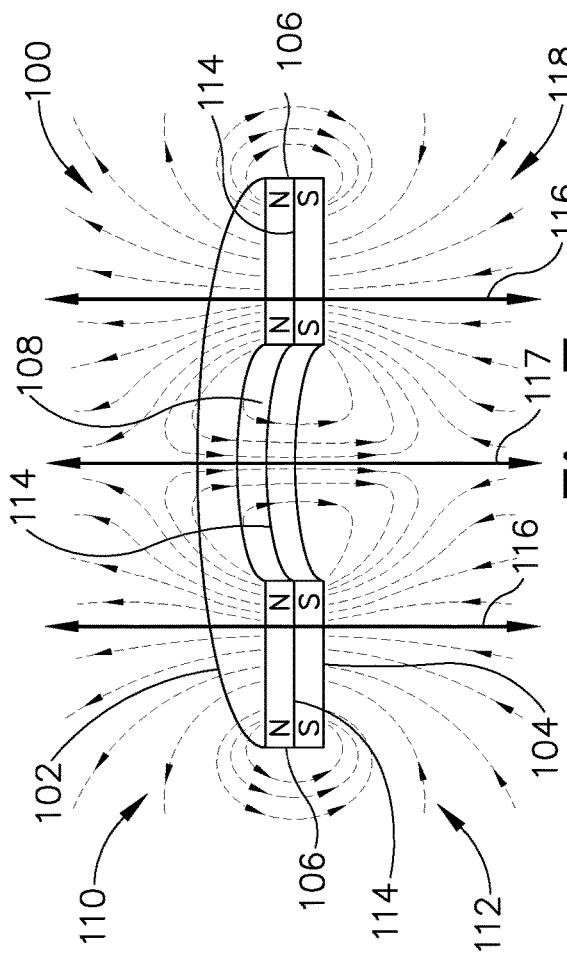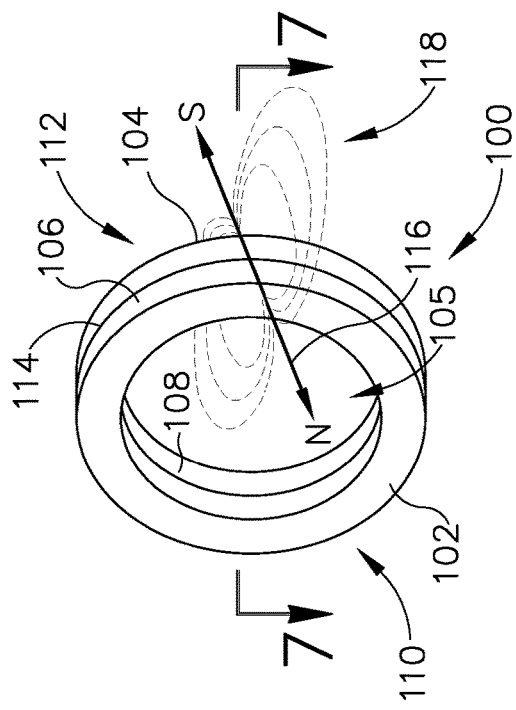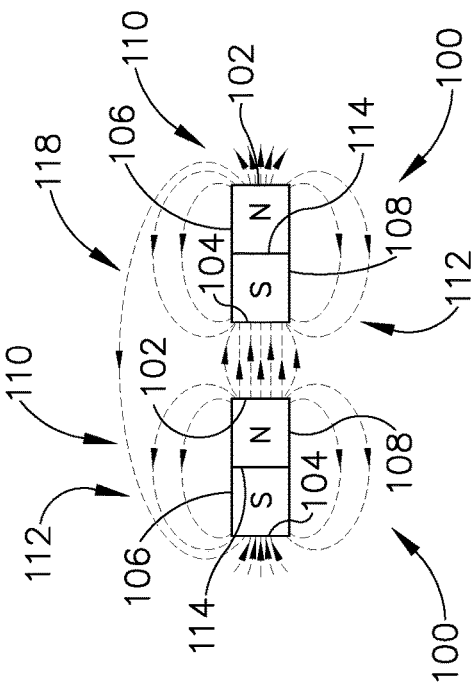

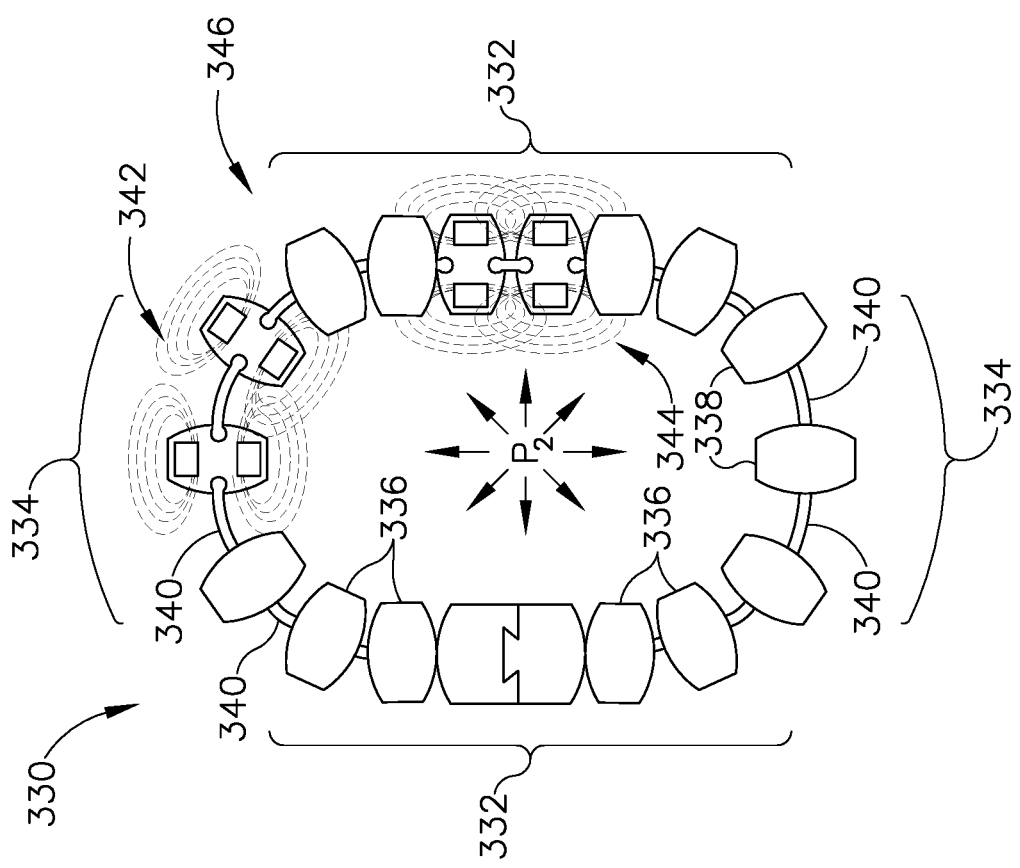
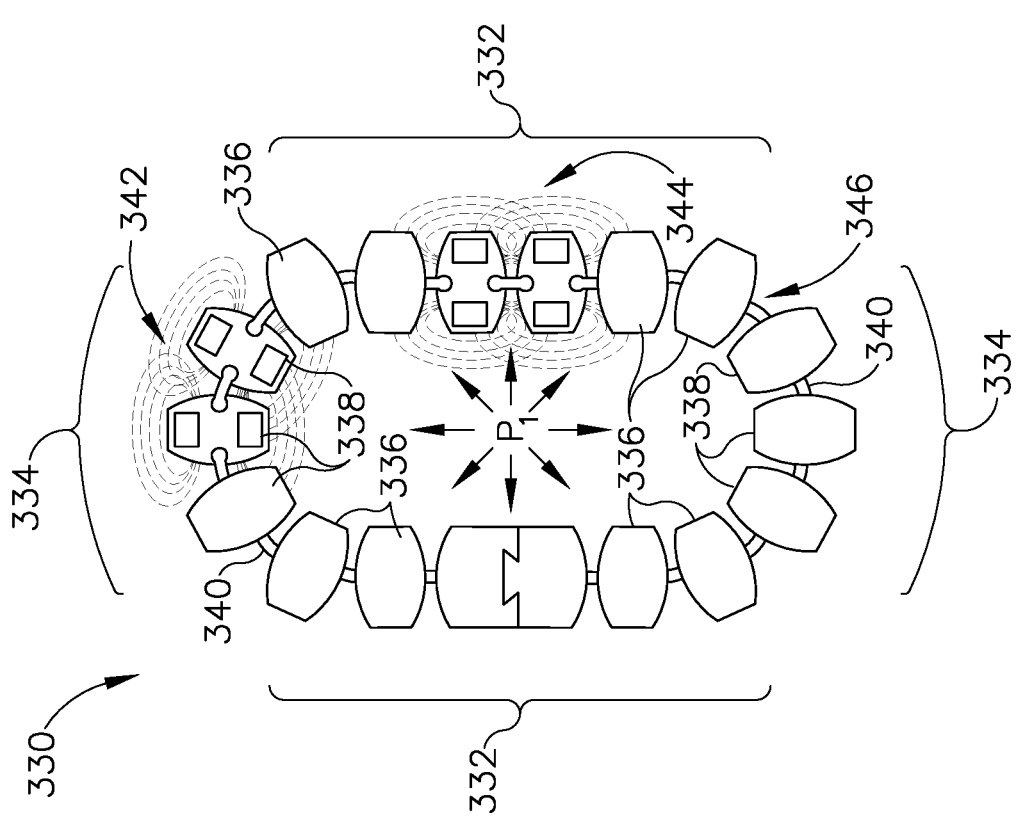

US 10,842,496 B2

IMPLANTABLE SPHINCTER ASSISTANCE DEVICE WITH TUNED MAGNETIC FEATURES

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a perspective view of an alternative magnet that may be readily incorporated into the sphincter augmentation device of FIG. 3;

FIG. 7 depicts a cross-sectional perspective view of the magnet of FIG. 6;

FIG. 8 depicts a cross-sectional view of two magnets of FIG. 6 aligned with opposite poles directed adjacent to one another;

FIG. 26 depicts a top plan view of an alternative sphincter augmentation device is a contracted configuration, with selected portions cut away for further clarity;

FIG. 27 depicts a top plan view of the sphincter augmentation device of FIG. 26, in a slightly expanded configuration, with selected portions cut away for further clarity;

Figure 1:
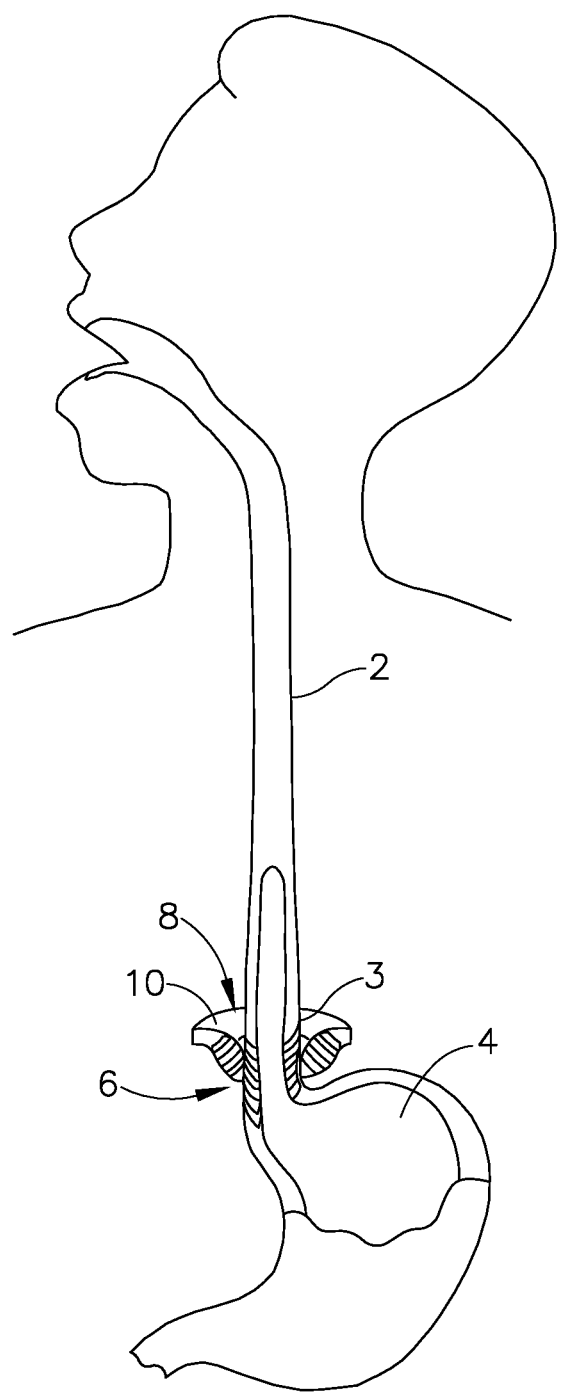
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Sphincter Augmentation Device

Figure 2:
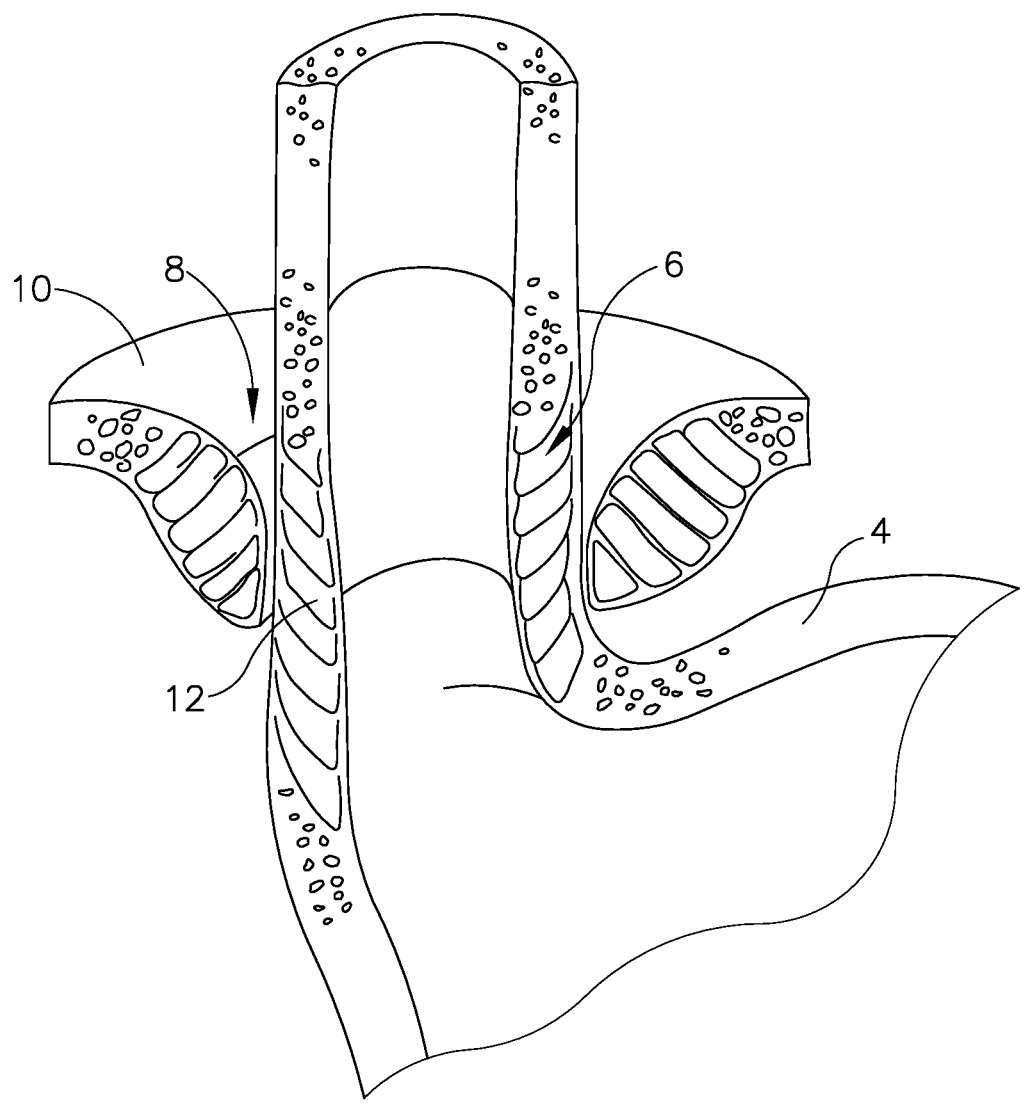
FIG. 2 depicts a cross-sectional isometric view, taken along a coronal plane of the body, of a human esophagogastric junction.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 3:
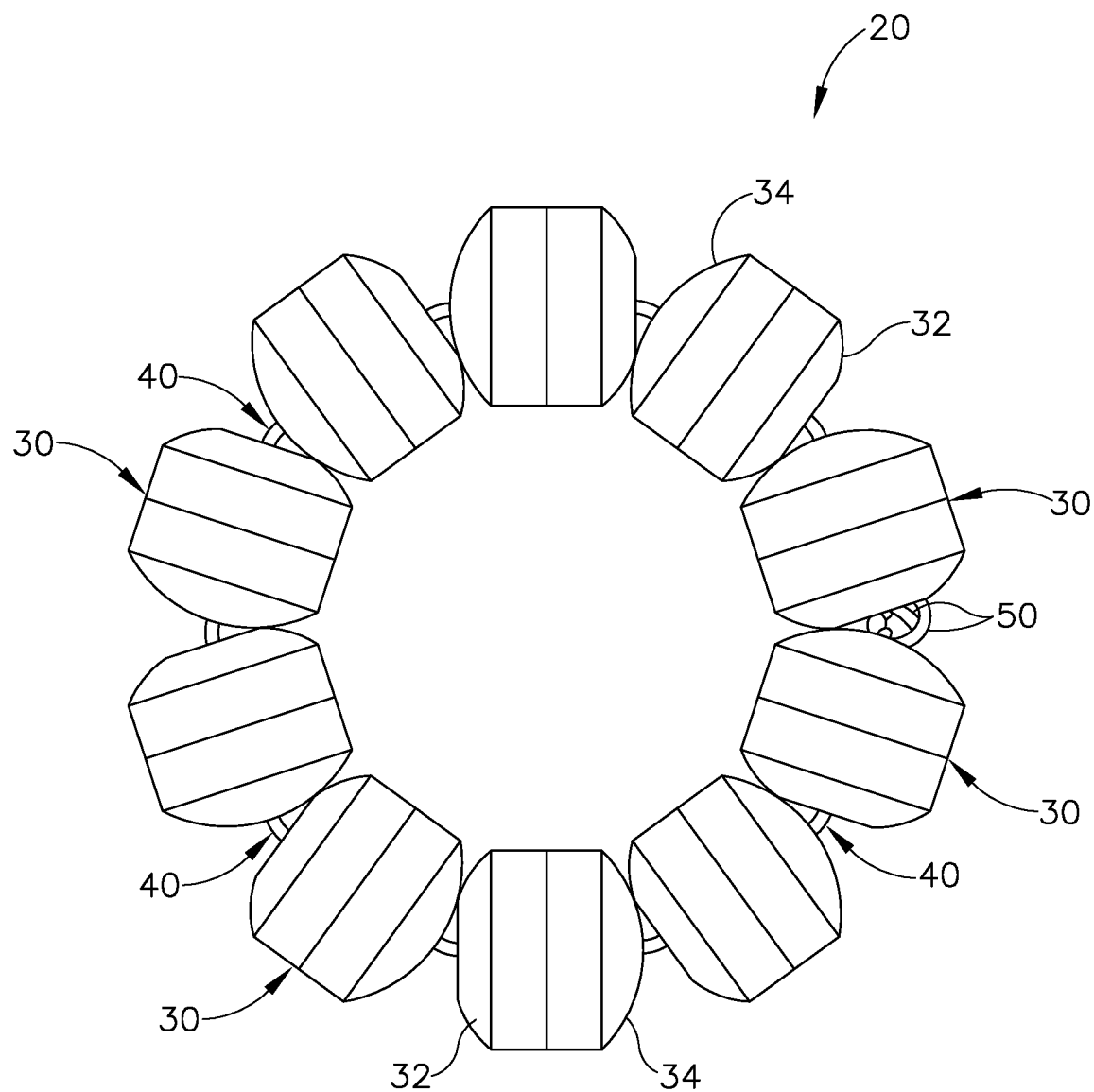
FIG. 3 depicts a top plan view of an exemplary sphincter augmentation device.
Figure 4:
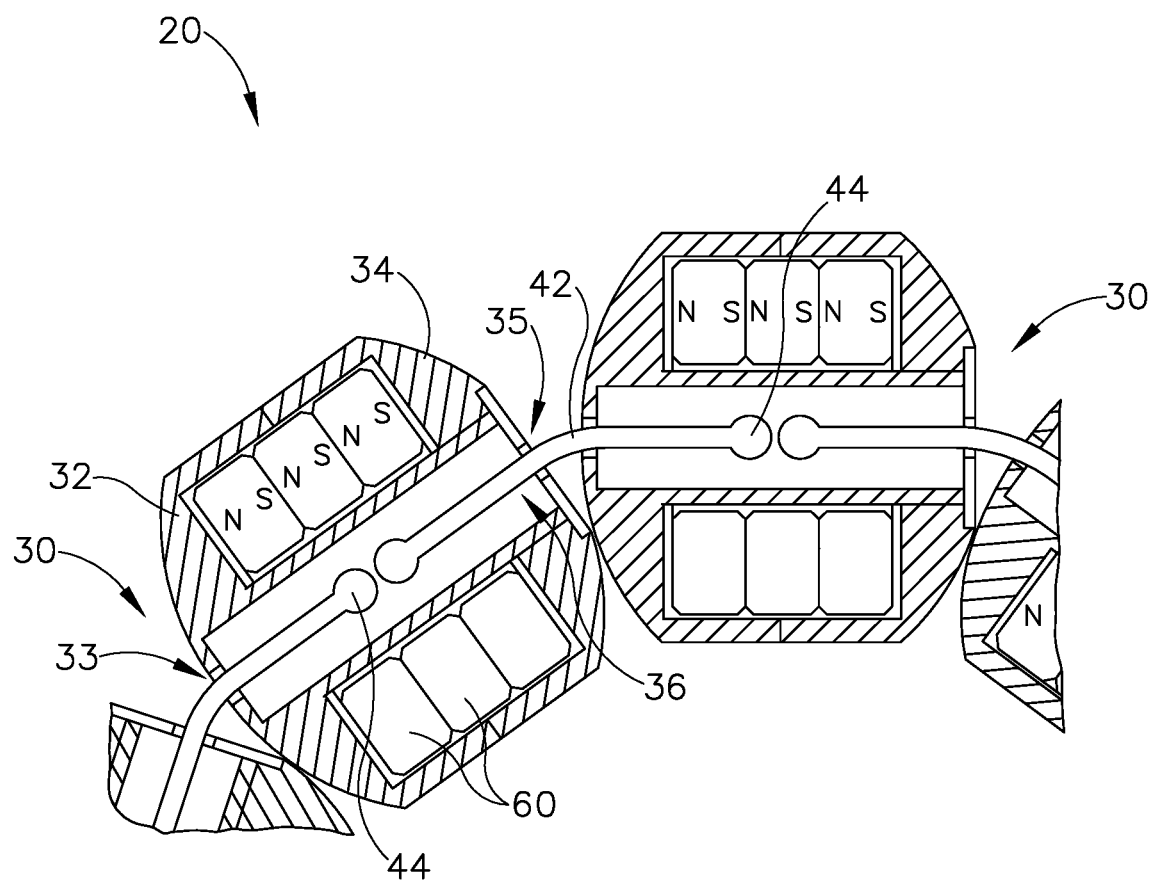
FIG. 4 depicts a partial, cross-sectional view of a portion of the sphincter augmentation device of FIG. 3.

FIGS. 3-5B show an exemplary sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in another bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
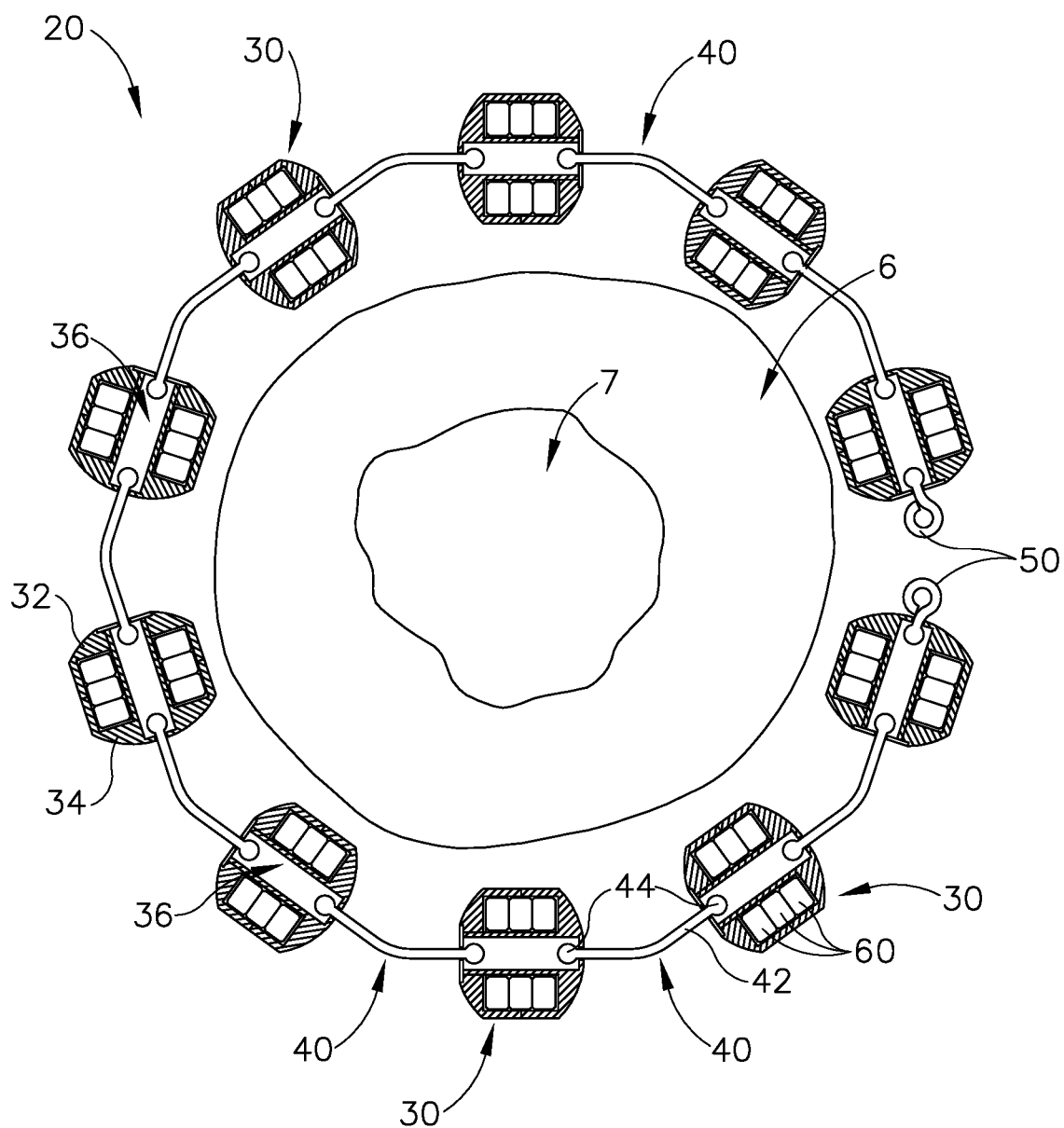
FIG. 5A depicts a top, cross-sectional view of the sphincter augmentation device of FIG. 3 positioned about an LES, with the sphincter augmentation device in an open and expanded configuration.
Figure 5B:
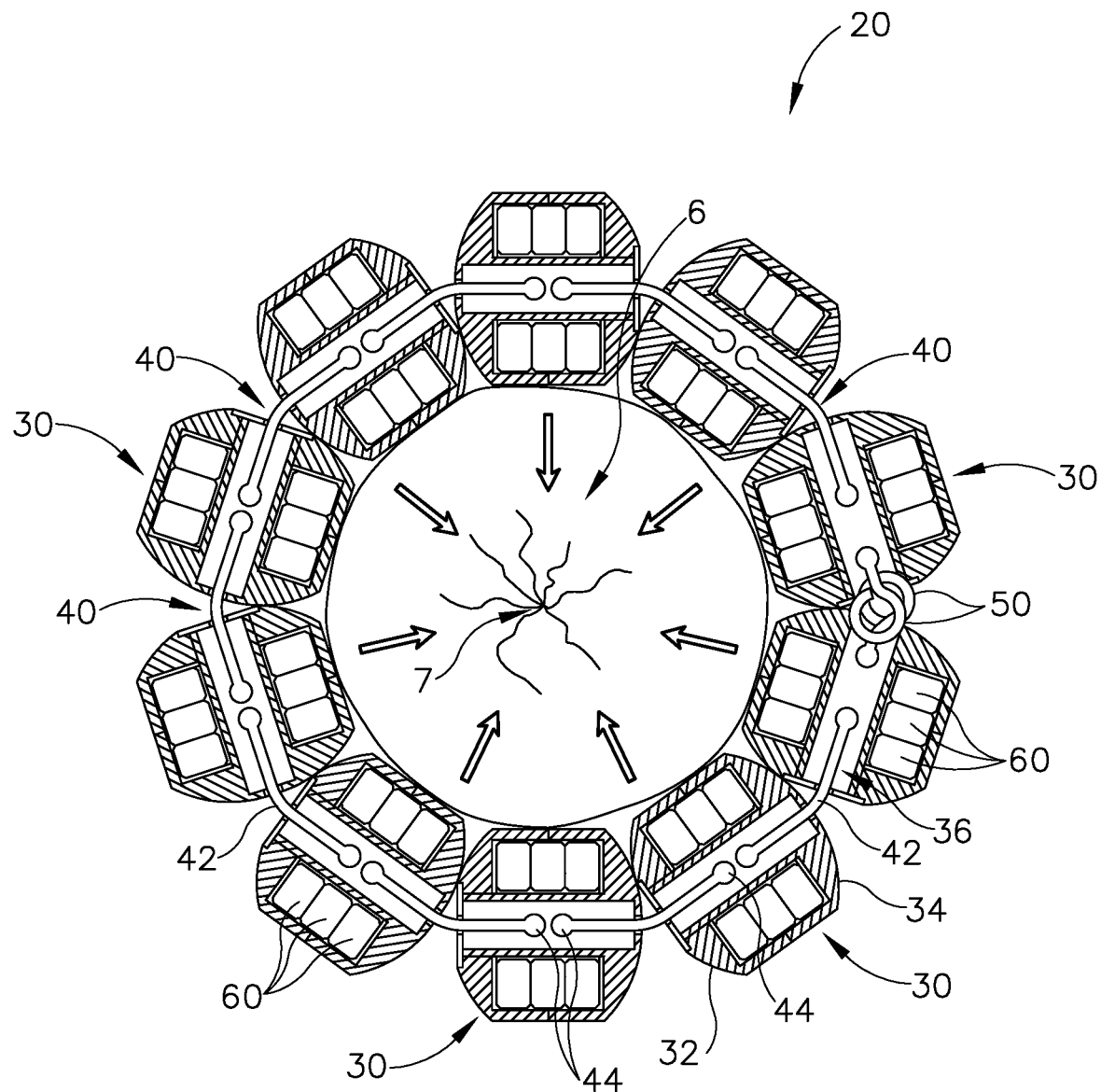
FIG. 5B depicts a top, cross-sectional view of the sphincter augmentation device of FIG. 3 positioned about the LES of FIG. 5A, with the sphincter augmentation device in a closed and contracted configuration.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be constructed and operable in accordance with at least some of the teachings of U.S. Pat. No. 7,695,427, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein.

II. Exemplary Sphincter Augmentation Devices with Tuned Magnetic Features

As mentioned above, magnets (60) are oriented within beads (30) such that each bead (30) will be magnetically attracted to the adjacent bead (30) in device (20), thereby biasing device (20) toward the contracted state during exemplary use, as shown in FIG. 5B. As also shown in FIG. 5B, exterior portions to adjacent beads (30) are dimensioned to abut against each other in the contracted state, which may help define the overall structure of device (20) in the contracted state. When device (20) is suitably coupled with LES (6), the tesla value between magnets (60) may be high enough to maintain opening (7) in a closed state to the point of preventing undesirable conditions that may be associated with a persistently open opening (7), but low enough such that beads (30) may move radially outwardly relative to each other by sliding along links (40), thereby effectively expanding device (20) to accommodate passage of a bolus of food, etc. through opening (7) of LES (6). Therefore, device (20) may repeatably transition between the contracted state and an expanded state while suitably attached to LES (6).

When device (20) repeatably transitions between the contracted state and the expanded state, it may be desirable to control the alignment of beads (30) relative to one another as device (20) transitions between the expanded state and the contracted state, or when device (20) experiences other external forces. Additionally, it may be desirable to control the forces device (20) imparts on LES (6) due to the magnetic attraction between adjacent beads (30) while device (20) is in the contracted state, the expanded state, and all other configurations therebetween.

One manner to accurately control the alignment of beads (30) and the forces device (20) imparts on LES (6) as mentioned above may be to form, modify, or otherwise "tune" magnets (60) to control the magnetic field vectors generated by individual magnets (60) relative to respective and/or adjacent beads (30). Another manner to accurately control the alignment of beads (30) and the forces device (20) imparts on LES (6) as mentioned above may be to align, form, modify, or otherwise "tune" magnets (60) within adjacent beads (30) to control magnetic field vectors generated by the interaction of magnets (60) within adjacent beads (30). Another manner to accurately control the alignment of beads (30) and the forces device (20) imparts on LES (6) as mentioned above may be to align or otherwise strategically orient the above-mentioned magnetic field vectors in relation to the contact surfaces, or any other suitable alignment features, of beads (30). It should be understood the term "vector" is used to represent a quantity having a magnitude and a direction. Therefore, when referencing any type of change and/or difference in a vector or a field of vectors, it should be understood this change and/or difference might be in magnitude and/or direction. The term "tune" may encompass any suitable means, as would be apparent to one having ordinary skill in the art in view of the teachings herein, to control (or otherwise dictate) the flux, magnitude, or direction of a magnetic field, and its corresponding vectors.

Strategically controlling magnitude and/or direction of magnetic field vectors generated by magnets (60) (i.e. "tuning") may allow more accurate control of the shape of device (20) as device (20) transitions between the expanded state and the contracted state. Additionally, controlling the direction and intensity of magnetic fields generated by magnets (60) may allow more accurate control of radial forces imparted on LES (6) while device (20) is in the various states/configurations described above.

A. Exemplary Magnets and Beads with Features for Coupling Magnetic Fields with Geometric Features of Beads FIGS. 6-7 show an alternative magnet (100) that may be readily incorporated into beads (30) in replacement of magnets (60) described above. In some instances, an individual magnet (100) may be placed within bead (30) instead of the plurality of magnets (60) described above. In such instances, a north pole section (110) may be adjacent to one opening (33) of bead (30) while a south pole section (112) may be adjacent to the opposite opening (35) of bead (30). In other instances, a plurality of magnets (100) may be "stacked" together within bead (30) in an end-to-end fashion. In such an instant, the plurality of magnets (100) may be aligned such that north pole section (110) of one magnet (100) is adjacent to one opening (33), while south pole section (112) of another magnet (100) is adjacent to the opposite opening (35) of bead (30). Of course, in either instance, magnets within adjacent beads (30) may be aligned such in a north-south relationship such that adjacent beads (30) are magnetically attracted to each other in accordance with the description above.

Magnet (100) is generally annular in shape defining an opening (105) dimensioned to receive a portion of housing(s) (32, 34) defining chamber (36). Magnet (100) includes a first annular axially presented surface (102), a second annular axially presented surface (104), a radially outwardly facing curved surface (106), and a radially inwardly facing curved surface (108) defining opening (105). Magnet (100) is axially magnetized such that the direction of magnetism extends from second annular axially presented surface (104) toward first annular axially presented surface (102). Therefore, magnet (100) is divided into north pole section (110) and south pole section (112) such that first annular axially presented surface (102) is entirely north pole section (110) and second annular axially presented surface (104) is entirely south pole section (112). North pole section (110) and south pole section (112) are separated by a neutral border (114) such that outer facing curved surface (106) and inner facing curved surface (108) possess both north pole sections (110) and south pole sections (112).

As shown in FIGS. 7-8, axially presented surfaces (102, 104) of north pole section (110) and south pole section (112), respectively, are substantially flat and planar and connect to both outer facing curved surface (106) and inner facing curved surface (108). Magnet (100) produces/attracts magnetic field vectors (118). As best seen in FIG. 7, when magnet (100) is isolated by itself (i.e. is a suitable distance from other magnetic fields), field vectors (118) extend away from north pole section (110) and are attracted toward south pole section (112). As also best seen in FIG. 7, some field vectors (118) bend due to the magnetic attraction between polar sections (110, 112). The specific bend of field vectors (118) may be defined by the geometric shape of magnet (100). In particular, field vectors (118) bend due to the relationship and shape of north pole section (110) and south pole section (112). Therefore, field vectors (118) emitted from portions of north pole section (110) that are close to south pole section (112) tend to bend toward south pole section (112) to form a closed loop; while field vectors (118) emitted from portions of north pole section (110) that are further way from south pole section (112) are influenced by a lesser extent, thereby weakening the respective bend of field vectors (118) and/or not closing a loop.

Magnet (100), when isolated by itself from other magnetic fields, includes a plurality of magnetic field boundaries (116, 117). Due to the shape of magnet (100), field vectors (118) bending toward a magnetic field boundary (116, 117) do not cross such magnetic field boundary (116, 117). In the current example, there is a linear, central magnetic field boundary (117) extending along the central axis of magnet (100); and a cylindrical magnetic field boundary (116) spaced a predetermined radial distance from the central magnetic field boundary (117).

As shown in FIG. 8, if two magnets (100) are positioned adjacent to each other such that first annular axially presented surface (102) of one magnet (100) is directly adjacent to second annular axially presented surface (104) of a second magnet (100), the magnetic field vector (118) of each magnet (100) is altered by the presence of one another. In particular, the magnetic field vector (118), and its associated magnetic flux, is strongest between first annular axially presented surface (102) of the first magnet (100) (the magnet (100) on the left), and second annular axially presented surface (104) of the second magnet (100) (the magnet (100) on the right). The distance between surfaces (102, 104) of magnets (100) plays a role in the magnetic force that attracts the two magnets (100) together. In some instances, such as when incorporated within beads (30) of device (20), the direction of the strongest magnetic field vectors (118) between directly adjacent annular axially presented surfaces (102, 104) maybe important as well. In the present example shown in FIG. 8, the strongest magnetic field vectors (118) are perpendicular to surfaces (102, 104). If magnets (100), as shown in FIG. 8, are housed in separate, directly adjacent beads (30), it may be beneficial to align the magnetic field vectors (118) such that a suitable amount of magnetic field vectors (118) suitably align with contacts surfaces of beads (30).

Figure 12:
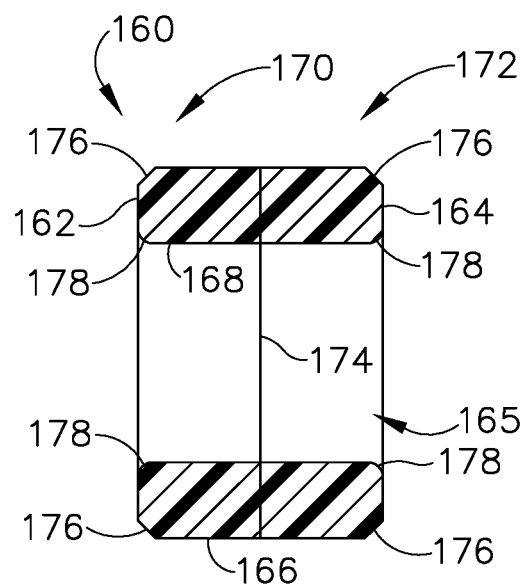
FIG. 12 depicts a cross-sectional view of the alternative magnet of FIG. 9
Figure 16:
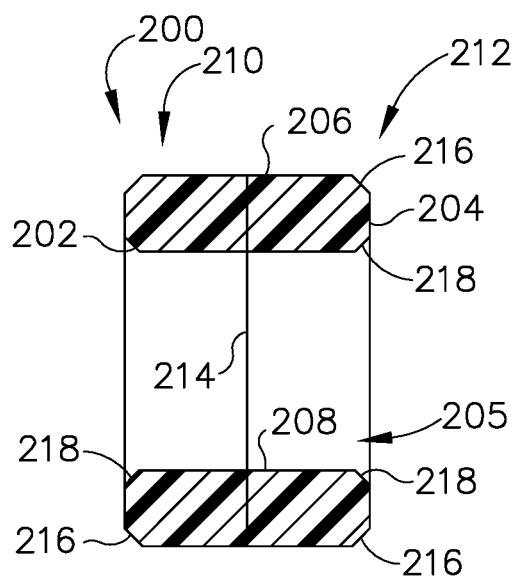
FIG. 16 depicts a cross-sectional view of the alternative magnet of FIG. 13.
Figure 20:
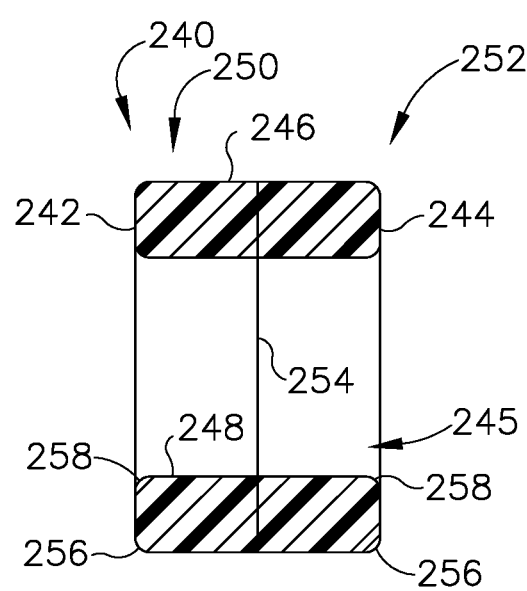
FIG. 20 depicts a cross-sectional view of the alternative magnet of FIG. 17.

FIGS. 12, 16, and 20 show various alternative magnets (160, 200, 240) that may be readily incorporated into device (20) in replacement of magnets (60, 100) described above. In particular, magnets (160, 200, 240) may be coupled with alternative beads (150), which may also be readily incorporated into device (20) in replacement of beads (30) described above. As will be described in greater detail below, magnets (160, 200, 240) are shaped, formed, or otherwise "tuned" to direct respective magnetic fields (188, 228, 268) into suitable alignment with contact surfaces (158) of beads (150).

Beads (150) are substantially similar to beads (30) described above, with differences elaborated below. Each bead (150) includes a chamber (152), a pair of openings (154), which are substantially similar to chamber (36) and openings (33, 35) described above, respectively. Therefore, beads (150) are configured to slidably receive links (40) in order to expand and contract relative to each other in accordance with the description above. Each bead (150) includes a pair of contact surfaces (158) dimensioned to abut against contact surfaces (158) of adjacent beads (150) in the contracted state, similar to bead (30) described above. Additionally, each bead (150) defines a magnet chamber (156) dimensioned to house at least one magnet (160, 200, 240) in a similar orientation which bead (30) houses magnets (60). Therefore, magnets (60) are oriented within beads (150) such that each bead (150) will be magnetically attracted to the adjacent bead (150) in device (20). In other words, beads (150) are magnetically attracted to each other to magnetically bias device (20) toward the contracted configuration.

Figure 9:
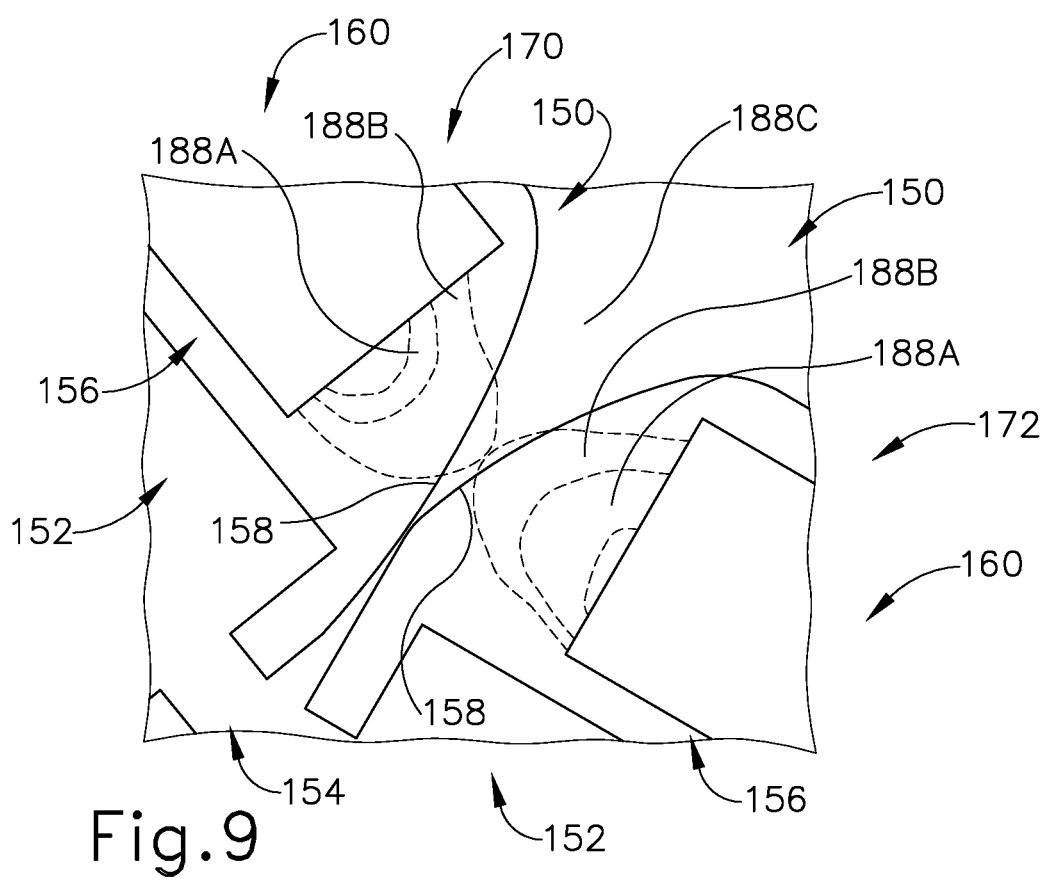
FIG. 9 depicts a cross-sectional view of a pair of alternative beads, each containing an alternative magnet, that may be readily incorporated into the sphincter augmentation device of FIG. 3.
Figure 10:
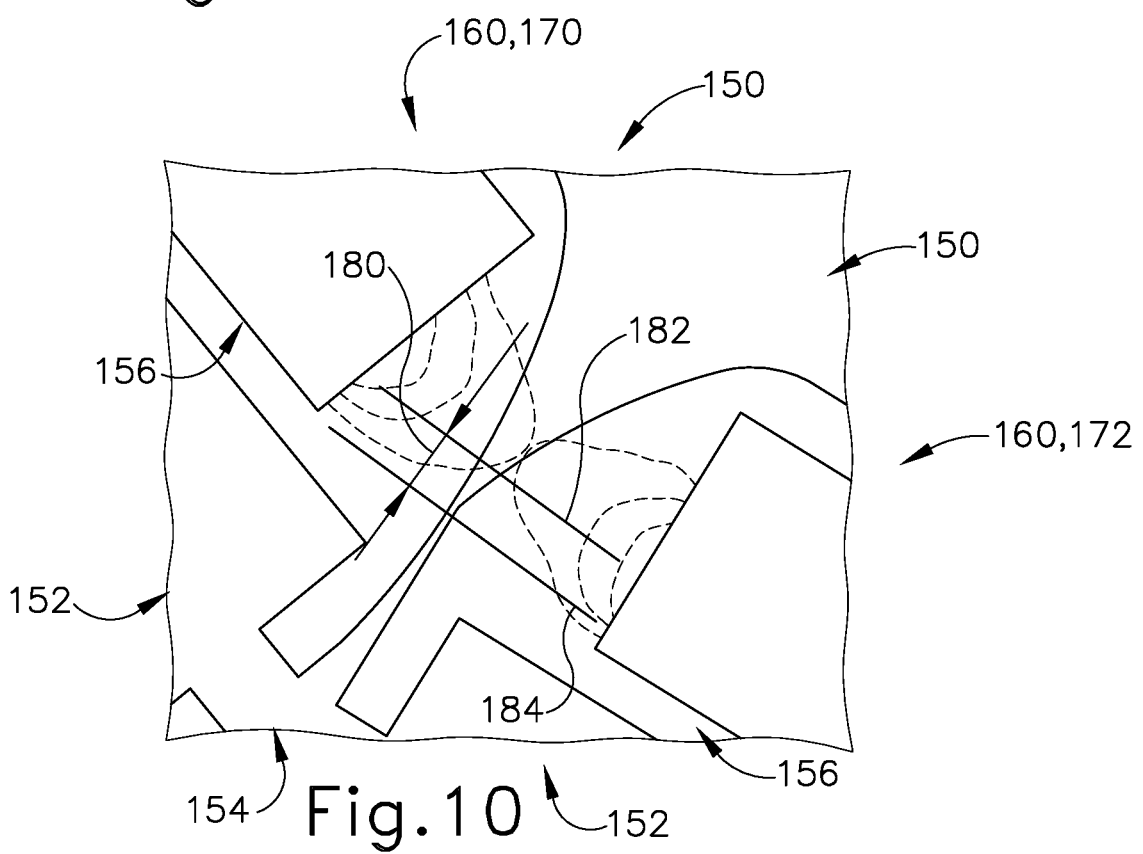
FIG. 10 depicts a cross-sectional view of the pair of beads and magnets of FIG. 9, further showing the distance between the center of contact of the pair of beads and the contact location the generated magnetic fields are trying to achieve.
Figure 11:
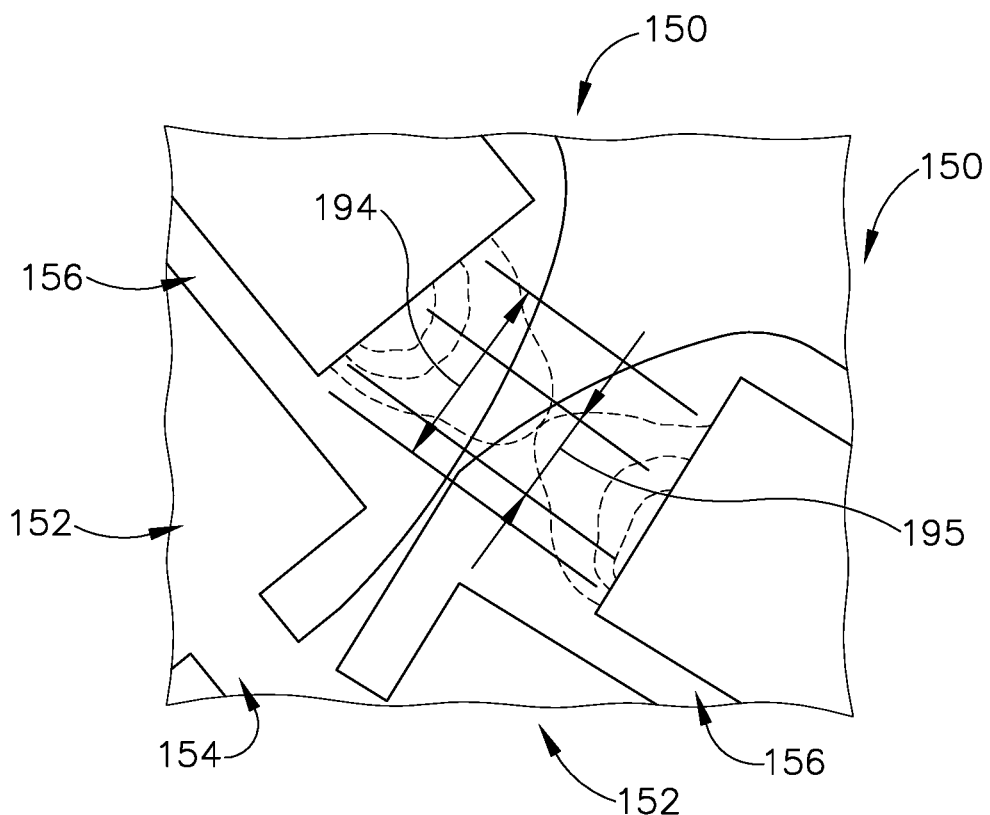
FIG. 11 depicts a cross-sectional view of the pair of beads and magnets of FIG. 9, further showing the width of the stronger portion of the generated magnetic field.

FIGS. 9-11 show an alternative magnet (160) readily incorporated into beads (150), which are readily incorporated into device (20) described above. Similar to magnets (60, 100) described above, an individual magnet (160) or a plurality of magnets (160) may be placed within bead (150) such that a north pole section (170) may be adjacent to one opening (154) of bead (30) while a south pole section (172) may be adjacent to the opposite opening (154) of bead (30). Magnets (160) within adjacent beads (150) may be aligned in a north-south relationship such that adjacent beads (150) are magnetically attracted to each other in accordance with the description above.

As best seen in FIG. 12, magnet (160) is generally annular in shape defining an opening (165) dimensioned to receive a portion of bead (150) defining chamber (152). Magnet (160) includes a first annular axially presented surface (162), a second annular axially presented surface (164), an outer facing curved surface (166), and an inner facing curved surface (168) defining opening (165); which may be substantially similar to first annular axially presented surface (102), second annular axially presented surface (104), outer facing curved surface (106), and inner facing curved surface (108) defining opening (105), respectively, with differences elaborated below.

Therefore, magnet (160) is axially magnetized such that the direction of magnetism extends from second annular axially presented surface (164) toward first annular axially presented surface (162). Therefore, magnet (160) is divided into north pole section (170) and south pole section (172) such that first annular axially presented surface (162) is entirely north pole section (170) and second annular axially presented surface (164) is entirely south pole section (172). North pole section (170) and south pole section (172) are separated by a neutral border (174) such that outer facing curved surface (166) and inner facing curved surface (168) possess both north pole sections (170) and south pole sections (172).

Axially presented surfaces (162, 164) of north pole section (170) and south pole section (172), respectively, are substantially flat and planar. However, unlike axially presented surfaces (102, 104) described above, axially presented surfaces (162, 164) each terminate into a respective chamfered outer diameter (176) and radiused inner diameter (178). In particular, chamfered outer diameters (176) connect axially presented surfaces (162, 164) with outer facing curved surface (166). Likewise, radiused inner diameters (178) connect axially presented surfaces (162, 164) with inner facing curved surface (168).

As best seen in FIG. 9, axially presented surfaces (162, 164) in combination with chamfered outer diameters (176) and radiused inner diameters (178) are suitably dimensioned to create a suitable magnetic field (188A, 188B, 188C) having a stronger portion of magnetic field (188A), an intermediary portion of magnetic field (188B), and a weakest portion of magnetic field (188C); where strongest portion of magnetic field (188A) and an intermediary magnetic field (188B) are suitably aligned with resting contact surfaces (158) of adjacent beads (150). In other words, the geometric profile of north pole sections (170) and south pole sections (172) of magnets (160) within adjacent beads (150) are configured to generate a focused magnetic field (188A, 188B) that is suitably aligned with resting contact surfaces for optimal operating conditions when beads (150) are incorporated into device (20) that is coupled with LES (6).

In some instances, at least a portion of magnetic fields (188A, 188B) are perpendicular with resting contact surfaces (158). Magnetic fields (188A, 188B) may have another suitable alignment relative to resting contact surfaces (158) as would be apparent to one having ordinary skill in the art in view of the teachings herein. The geometry of axially presented surfaces (162, 164) in combination with chamfered outer diameters (176) and radiused inner diameters (178) may be configured to generate sections of magnetic fields (188A, 188B, 188C), that are aligned with contact surfaces (158), configured to promote stability between adjacent beads (150) in the contracted state. Likewise, the geometry of axially presented surfaces (162, 164) in combination with chamfered outer diameters (176) and radiused inner diameters (178) may be configured to generate sections of magnetic fields (188A, 188B, 188C), that are aligned with contact surfaces (158), to promote beads (150) to impart suitable forces on LES (6) due to the magnetic attraction between adjacent beads (150) while device (20) is in the contracted state, the expanded state, and all other configurations therebetween. It should be understood that due to the focused direction of magnetic field (188A, 188B, 188C) relative to resting contact surfaces (158), the control of stability and imparted forces may be better controlled than by just designing device (20) around the distance between magnets (60) in adjacent beads (30).

FIG. 10 highlights a distance (180) between the physical center (184) of contact between contact surfaces (158) and the contact location (182) the magnetic fields (188A, 188B) are trying to achieve. FIG. 11 highlights the width (194) of the strongest portion of a magnetic field when there is no chamfered outer diameter (176) and radiused inner diameter (178), as compared to the width (195) of the strongest portions of magnetic field (188A, 188B, 188C) when chamfered outer diameter (176) and radiused inner diameter (178) are present. As noticed, the width (195) of the strongest portions of magnetic field (188A, 188B, 188C) is narrower and more precisely "tuned" as compared to the width (194) of the stronger position of a magnetic field without chamfered outer diameter (176) and radiused inner diameter (178). This may provide more accurately placement of beads (150) in the contracted state.

In some instances, radiused inner diameter (178) may have a dimension of 0.005 inches while chamfered outer diameter (176) may have a dimension of 0.015 inches. Of course, any other suitable dimension may be incorporated as would be apparent to one having ordinary skill in the art in view of the teachings herein. In other instances, inner diameter (178) portion may be chamfered, while outer diameter portion (176) may be radiused. In other instances, both outer diameter (176) and inner diameter (178) may be chamfered or radiused. Of course, outer diameter (176), inner diameter (178), and axially presented surfaces (162, 164) may have any suitable geometry as would be apparent to one having ordinary skill in the art in view of the teachings herein. For example, an axially presented surface (162, 164) may be convex, concave, undulating, step-like, zig-zag, etc.

Figure 13:
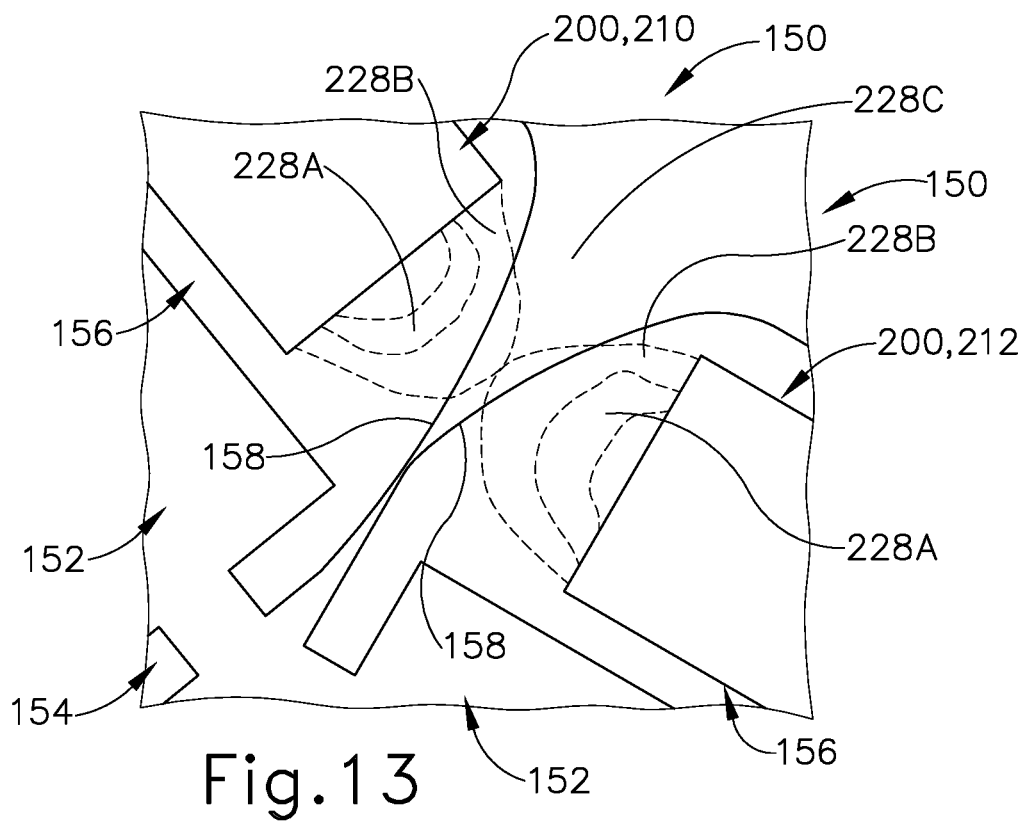
FIG. 13 depicts a cross-sectional view of the pair of beads of FIG. 9, each containing an alternative magnet, that may be readily incorporated into the sphincter augmentation device of FIG. 3.
Figure 14:
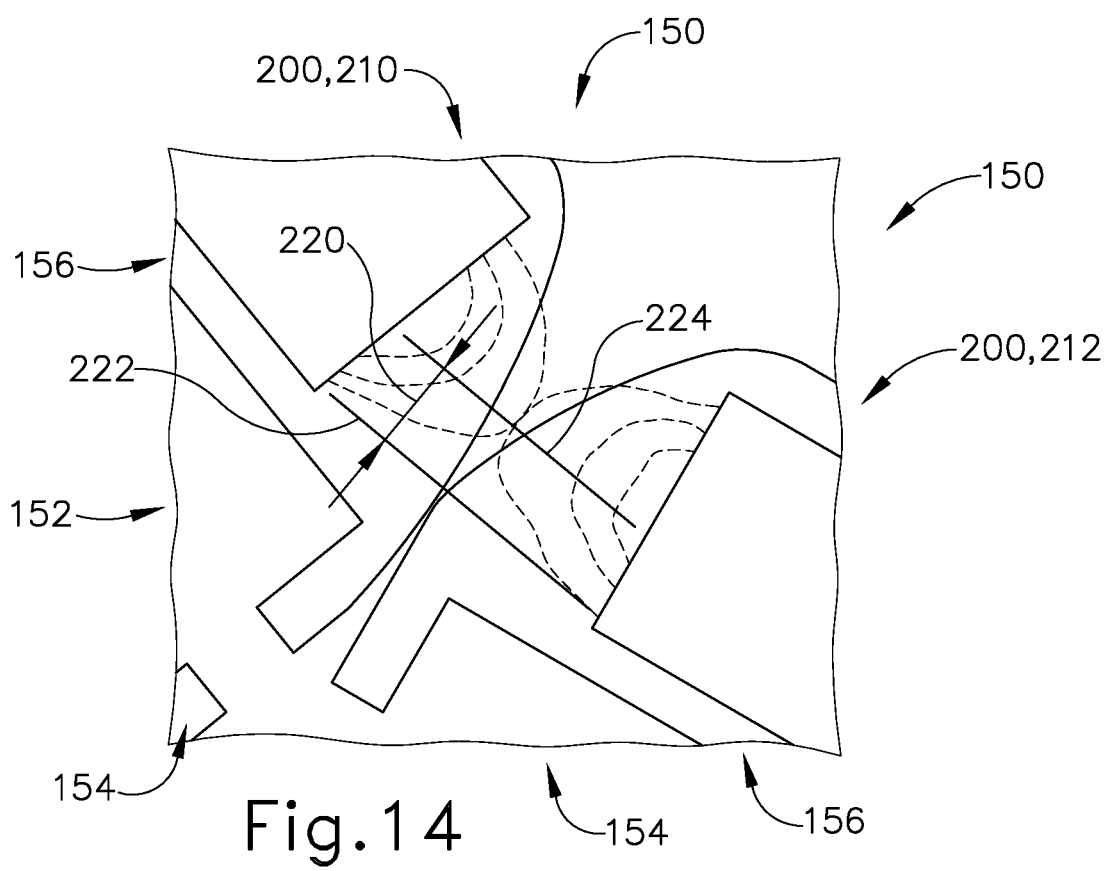
FIG. 14 depicts a cross-sectional view of the pair of beads and magnets of FIG. 13, further showing the distance between the center of contact of the pair of beads and the contact location the generated magnetic fields are trying to achieve.
Figure 15:
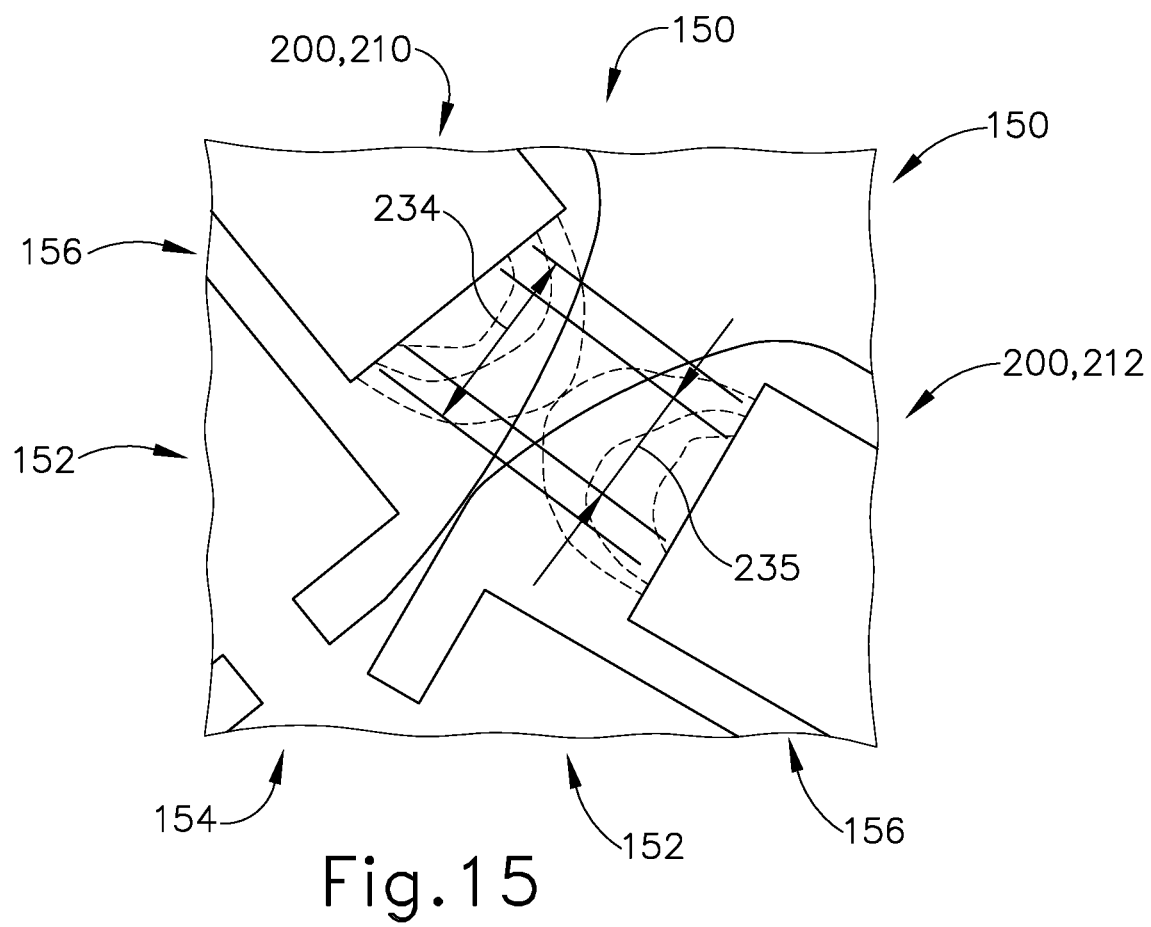
FIG. 15 depicts a cross-sectional view of the pair of beads and magnets of FIG. 13, further showing the width of the stronger portion of the generated magnetic field.

FIGS. 13-15 show an alternative magnet (200) readily incorporated into beads (150), which are readily incorporated into device (20) described above. Similar to magnets (60, 100, 160) described above, an individual magnet (200) or a plurality of magnets (200) may be placed within bead (150) such that a north pole section (210) may be adjacent to one opening (154) of bead (30) while a south pole section (212) may be adjacent to the opposite opening (154) of bead (30). Magnets (200) within adjacent beads (150) may be aligned in a north-south relationship such that adjacent beads (150) are magnetically attracted to each other in accordance with the description above.

As best seen in FIG. 16, magnet (200) is generally annular in shape defining an opening (205) dimensioned to receive a portion of bead (150) defining chamber (152). Magnet (200) includes a first annular axially presented surface (202), a second annular axially presented surface (204), an outer facing curved surface (206), and an inner facing curved surface (208) defining opening (205); which may be substantially similar to first annular axially presented surface (102), second annular axially presented surface (104), outer facing curved surface (106), and inner facing curved surface (108) defining opening (105), respectively, with differences elaborated below.

Therefore, magnet (200) is axially magnetized such that the direction of magnetism extends from second annular axially presented surface (204) toward first annular axially presented surface (202). Therefore, magnet (200) is divided into north pole section (210) and south pole section (212) such that first annular axially presented surface (202) is entirely north pole section (210) and second annular axially presented surface (204) is entirely south pole section (212). North pole section (210) and south pole section (212) are separated by a neutral border (214) such that outer facing curved surface (206) and inner facing curved surface (208) possess both north pole sections (210) and south pole sections (212).

Axially presented surfaces (202, 204) of north pole section (210) and south pole section (212), respectively, are substantially flat and planar. However, unlike axially presented surfaces (102, 104) described above, axially presented surfaces (202, 204) each terminate into a respective chamfered outer diameter (216) and chamfered inner diameter (218). In particular, chamfered outer diameters (216) connect axially presented surfaces (202, 204) with outer facing curved surface (206). Likewise, chamfered inner diameters (218) connect axially presented surfaces (202, 204) with inner facing curved surface (208).

As best seen in FIG. 13, axially presented surfaces (202, 204) in combination with chamfered outer diameters (216) and chamfered inner diameters (218) are suitably dimensioned to create a suitable magnetic field (228A, 228B, 228C) having a stronger portion of magnetic field (228A), an intermediary portion of magnetic field (228B), and a weakest portion of magnetic field (228C); where strongest portion of magnetic field (228A) and an intermediary magnetic field (228B) are suitably aligned with resting contact surfaces (158) of adjacent beads (150). In other words, the geometric profile of north pole sections (210) and south pole sections (212) of magnets (200) within adjacent beads (150) are configured to generate a focused magnetic field (228A, 228B) that is suitably aligned with resting contact surfaces for optimal operating conditions when beads (150) are incorporated into device (20) that is coupled with LES (6).

In some instances, at least a portion of magnetic fields (228A, 228B) are perpendicular with resting contact surfaces (158). Magnetic fields (228A, 228B) may have another suitable alignment relative to resting contact surfaces (158) as would be apparent to one having ordinary skill in the art in view of the teachings herein. The geometry of axially presented surfaces (202, 204) in combination with chamfered outer diameters (216) and chamfered inner diameters (218) may be configured to generate sections of magnetic fields (228A, 228B, 228C), that are aligned with contact surfaces (158), configured to promote stability between adjacent beads (150) in the contracted state. Likewise, the geometry of axially presented surfaces (202, 204) in combination with chamfered outer diameters (216) and chamfered inner diameters (218) may be configured to generate sections of magnetic fields (228A, 228B, 228C), that are aligned with contact surfaces (158), to promote beads (150) to impart suitable forces on LES (6) due to the magnetic attraction between adjacent beads (150) while device (20) is in the contracted state, the expanded state, and all other configurations therebetween. It should be understood that due to the focused direction of magnetic field (228A, 228B, 228C) relative to resting contact surfaces (158), the control of stability and imparted forces may be better controlled than by just designing device (20) around the distance between magnets (60) in adjacent beads (30).

FIG. 14 highlights a distance (220) between the physical center (222) of contact between contact surfaces (158) and the contact location (224) the magnetic fields (228A, 228B) are trying to achieve. FIG. 15 highlights the width (234) of the strongest portion of a magnetic field when there are no chamfered outer diameters (216) and chamfered inner diameters (218), as compared to the width (235) of the strongest portions of magnetic field (228A, 228B, 228C) when chamfered outer diameters (216) and chamfered inner diameters (218) are present. As noticed, the width (235) of the strongest portions of magnetic field (228A, 228B, 228C) is narrower and more precisely "tuned" as compared to the width (234) of the stronger position of a magnetic field without chamfered outer diameters (216) and chamfered inner diameters (218). This may provide more accurately placement of beads (150) in the contracted state.

In some instances, chamfered diameters (216, 218) may have a dimension of 0.01 inches. Of course, any other suitable dimension may be incorporated as would be apparent to one having ordinary skill in the art in view of the teachings herein. In some instances, only inner diameter (218) or outer diameter (216) is chamfered, while the other simply connects to the respective curved surface (206, 208).

Figure 17:
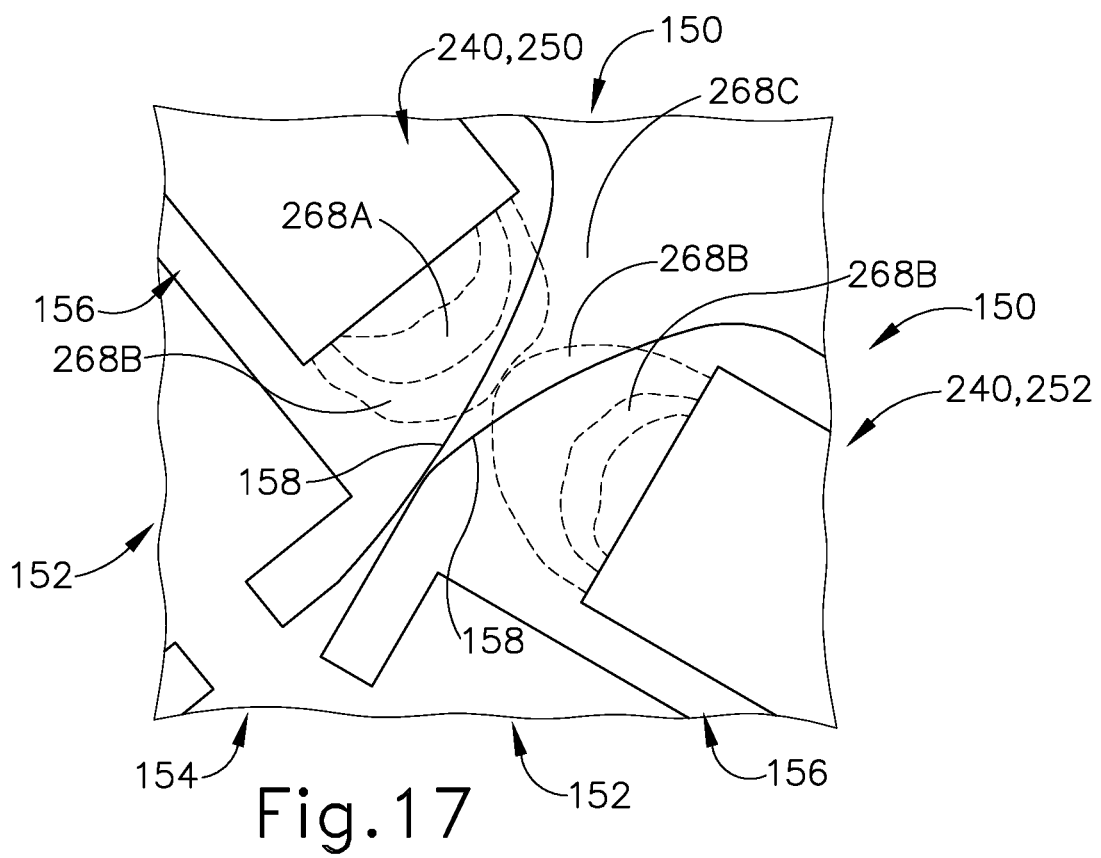
FIG. 17 depicts a cross-sectional view of the pair of beads of FIG. 9, each containing an alternative magnet, that may be readily incorporated into the sphincter augmentation device of FIG. 3.
Figure 18:
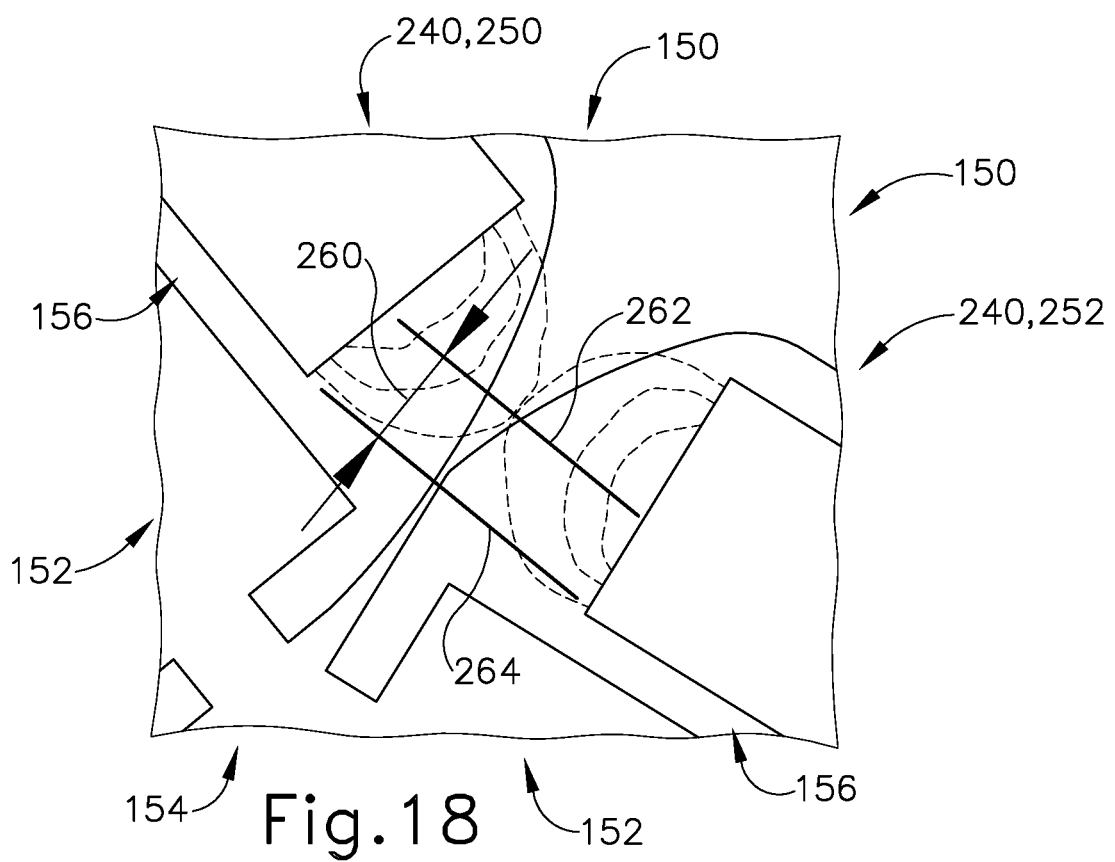
FIG. 18 depicts a cross-sectional view of the pair of beads and magnets of FIG. 17, further showing the distance between the center of contact of the pair of beads and the contact location the generated magnetic fields are trying to achieve.
Figure 19:
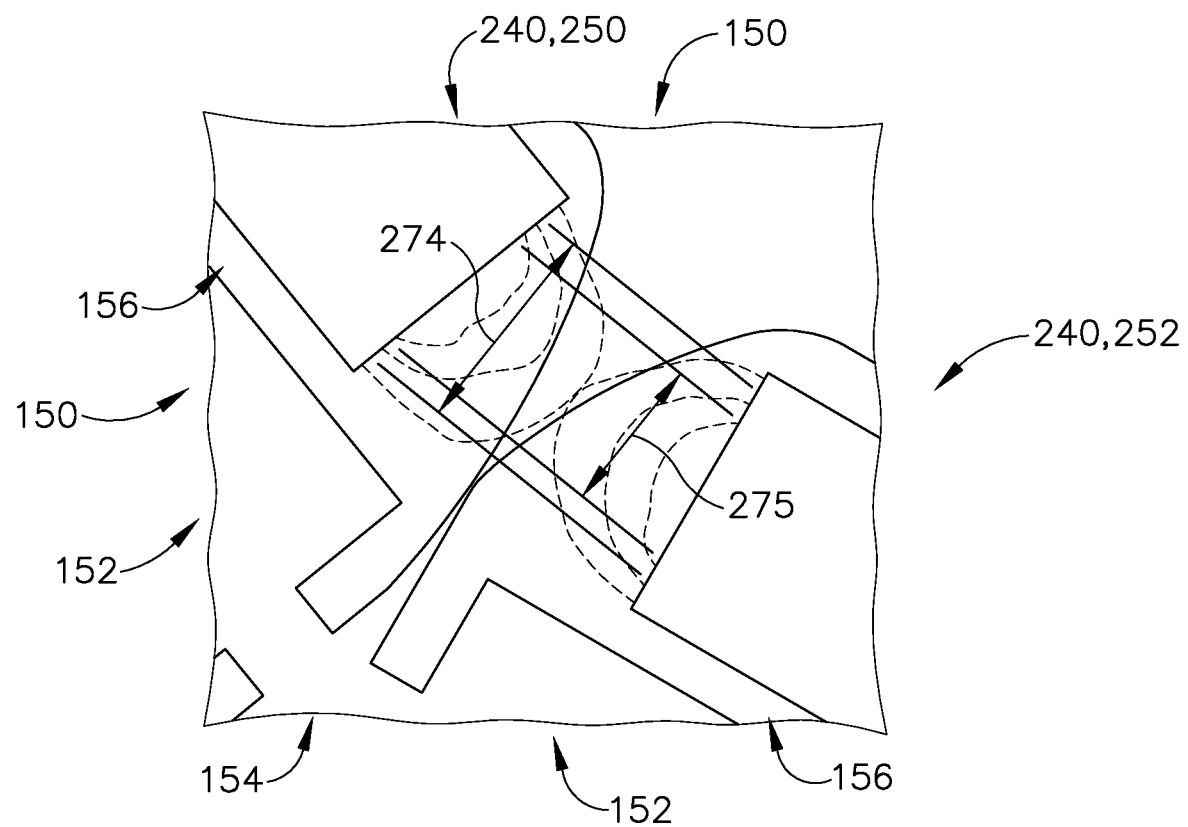
FIG. 19 depicts a cross-sectional view of the pair of beads and magnets of FIG. 17, further showing the width of the stronger portion of the generated magnetic field.

FIGS. 17-19 show an alternative magnet (240) readily incorporated into beads (150), which are readily incorporated into device (20) described above. Similar to magnets (60, 100, 160, 200) described above, an individual magnet (240) or a plurality of magnets (240) may be placed within bead (150) such that a north pole section (250) may be adjacent to one opening (154) of bead (30) while a south pole section (252) may be adjacent to the opposite opening (154) of bead (30). Magnets (240) within adjacent beads (150) may be aligned in a north-south relationship such that adjacent beads (150) are magnetically attracted to each other in accordance with the description above.

As best seen in FIG. 20, magnet (240) is generally annular in shape defining an opening (245) dimensioned to receive a portion of bead (150) defining chamber (152). Magnet (240) includes a first annular axially presented surface (242), a second annular axially presented surface (244), an outer facing curved surface (246), and an inner facing curved surface (248) defining opening (245); which may be substantially similar to first annular axially presented surface (102), second annular axially presented surface (104), outer facing curved surface (106), and inner facing curved surface (108) defining opening (105), respectively, with differences elaborated below.

Therefore, magnet (240) is axially magnetized such that the direction of magnetism extends from second annular axially presented surface (244) toward first annular axially presented surface (242). Therefore, magnet (240) is divided into north pole section (250) and south pole section (252) such that first annular axially presented surface (242) is entirely north pole section (250) and second annular axially presented surface (244) is entirely south pole section (252). North pole section (250) and south pole section (252) are separated by a neutral border (254) such that outer facing curved surface (246) and inner facing curved surface (248) possess both north pole sections (250) and south pole sections (252).

Axially presented surfaces (242, 244) of north pole section (250) and south pole section (252), respectively, are substantially flat and planar. However, unlike axially presented surfaces (102, 104) described above, axially presented surfaces (242, 244) each terminate into a respective radiused outer diameter (256) and radiused inner diameter (258). In particular, radiused outer diameters (256) connect axially presented surfaces (242, 244) with outer facing curved surface (246). Likewise, radiused inner diameters (258) connect axially presented surfaces (242, 244) with inner facing curved surface (248).

As best seen in FIG. 17, axially presented surfaces (242, 244) in combination with radiused outer diameters (256) and radiused inner diameters (258) are suitably dimensioned to create a suitable magnetic field (268A, 268B, 268C) having a stronger portion of magnetic field (268A), an intermediary portion of magnetic field (268B), and a weakest portion of magnetic field (268C); where strongest portion of magnetic field (268A) and an intermediary magnetic field (268B) are suitably aligned with resting contact surfaces (158) of adjacent beads (150). In other words, the geometric profile of north pole sections (250) and south pole sections (252) of magnets (240) within adjacent beads (150) are configured to generate a focused magnetic field (268A, 268B) that is suitably aligned with resting contact surfaces for optimal operating conditions when beads (150) are incorporated into device (20) that is coupled with LES (6).

In some instances, at least a portion of magnetic fields (268A, 268B) are perpendicular with resting contact surfaces (158). Magnetic fields (268A, 268B) may have another suitable alignment relative to resting contact surfaces (158) as would be apparent to one having ordinary skill in the art in view of the teachings herein. The geometry of axially presented surfaces (242, 244) in combination with radiused outer diameters (256) and radiused inner diameters (258) may be configured to generate sections of magnetic fields (268A, 268B, 268C), that are aligned with contact surfaces (158), configured to promote stability between adjacent beads (150) in the contracted state. Likewise, the geometry of axially presented surfaces (242, 244) in combination with radiused outer diameters (256) and radiused inner diameters (258) may be configured to generate sections of magnetic fields (268A, 268B, 268C), that are aligned with contact surface (158), to promote beads (150) to impart suitable forces on LES (6) due to the magnetic attraction between adjacent beads (150) while device (20) is in the contracted state, the expanded state, and all other configurations therebetween. It should be understood that due to the focused direction of magnetic field (268A, 268B, 268C) relative to resting contact surfaces (158), the control of stability and imparted forces may be better controlled than by just designing device (20) around the distance between magnets (60) in adjacent beads (30).

FIG. 18 highlights a distance (260) between the physical center (264) of contact between contact surfaces (158) and the contact location (262) the magnetic fields (268A, 268B) are trying to achieve. FIG. 19 highlights the width (274) of the strongest portion of a magnetic field when there are no radiused outer diameters (256) and radiused inner diameters (258), as compared to the width (275) of the strongest portions of magnetic field (268A, 268B, 268C) when radiused outer diameters (256) and radiused inner diameters (258) are present. As noticed, the width (275) of the strongest portions of magnetic field (268A, 268B, 268C) is narrower and more precisely "tuned" as compared to the width (274) of the stronger position of a magnetic field without radiused outer diameters (256) and radiused inner diameters (258). This may provide more accurately placement of beads (150) in the contracted state.

In some instances, radiused diameters (256, 258) may have a dimension of 0.005 inches. Of course, any other suitable dimension may be incorporated as would be apparent to one having ordinary skill in the art in view of the teachings herein. In some instances, only inner diameter (218) or outer diameter (216) is radiused, while the other simply connects to the respective curved surface (206, 208).

It may be desirable to ensure device (20), or any suitable device mentioned herein, generates a cumulative constrictive pressure that can prevent gastric fluid from passing the LES (6). The resulting magnetic field flux density necessary to create 15 mm/Gg-25 mm/Hg of pressure between a bead (30, 150) and exterior of esophagus (2) is 0.4-0.6 tesla at the focal point and diminishes to 0.2-/0.1 tesla as you move away from the focal point. This would provide a function range of magnetic flux density of 0.05-0.8 tesla with the ideal magnetic flux density in the range of 0.2-0.6 tesla in the constricted configuration.

Figure 21:
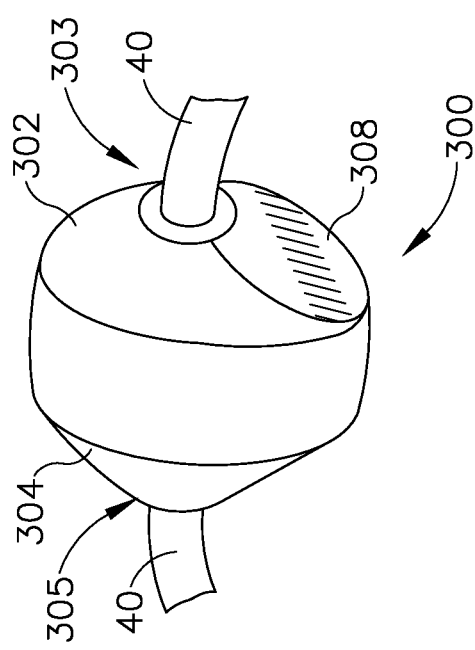
FIG. 21 depicts a perspective view of an alternative bead that may be readily incorporated into the sphincter augmentation device of FIG. 3.
Figure 22:
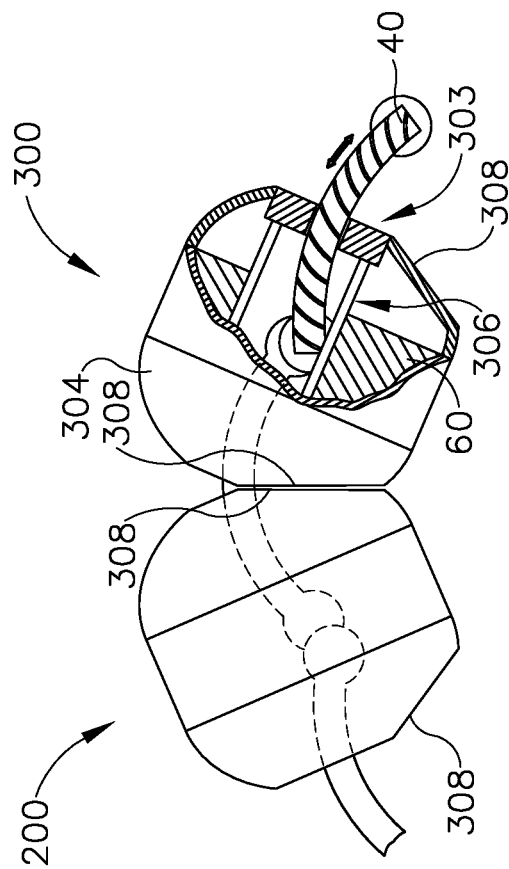
FIG. 22 depicts a top plan view of the bead of FIG. 21, with selected portions of a casing cut away to reveal internal structures.

As mentioned above, it may be desirable to "tune" a magnet (60, 100, 160, 200, 240) such that the generated magnetic fields are aligned with resting contact surfaces (158) of beads (150) in the contracted state. Therefore, in some instances, it may be desirable to provide a surface contact area that is aligned to the interfacing features between adjacent beads (150) in a contracted state. FIGS. 21-22 show an alternative bead (300) that may be readily incorporated into device (20) in replacement of beads (30, 150) described above. Beads (300) may be substantially similar to beads (30, 150) described above, with differences described below. Therefore, each bead (300) may house at least one magnet (60, 100, 160, 200, 240). Additionally, each bead (300) defines a chamber (306) and include a first housing (302) defining an opening (303), and a second housing (304) defining an opening (305); which may be substantially similar to chamber (36), housing (32) defining opening (33), and housing (34) defining opening (35) described above respectively. Therefore, chamber (36) may slidingly house a portion of link (40) such that link (40) may connect adjacent beads (300).

Additionally, each bead (300) has a pair of substantially flat contact surfaces (308). Contact surfaces (308) are enlarged and configured to abut against directly adjacent contact surfaces (308) when device (20) opens in the contracted configuration. The large flat contact surface (308) may provide a larger plane of alignment to allow magnetic fields (118, 188, 228, 268) to more easily align relative to adjacent beads (300), thereby providing more control and stability. It may be desirable to align the center of magnetic fields (118, 188, 228, 268) with the center of the contact surface (308). In the current example, contact surfaces (308) extend along a plane that goes through a central point of device (20). However, this is merely optional, as contact surfaces (308) may extend along any suitable plane as would be apparent to one having ordinary skill in the art in view of the teachings herein. Contact surfaces (308) may terminate a suitable distance from the inner diameter portion of bead (300) such that contact surfaces (308) may be less likely to pinch or otherwise harm tissue which device (20) surrounds. Contact surfaces (308) may have any suitable complementary geometry to promote locking between beads (300) when device is in a contracted state. For instance, contact surface (308) may have complementary undulating ribs configured to lock against adjacent contact surfaces (308) in the contracted state, thereby promoting stability.

B. Magnetic Features to Promote Variable Magnetic Field Strengths within Sphincter Augmentation Devices In some instances, it may be desirable to "tune" a magnetic field within device (20) by controlling and varying the magnetic field strength within different beads (30, 150, 300). Controlling and varying the magnetic field strengths within different beads (30, 150, 300) may allow for better control of the profile of device (20) in the contracted state. In some instances, is may be desirable to allow a magnet (60, 100, 160, 200, 240) to float within a respective magnetic chamber of bead (30, 150, 300) so that the magnetic field generated by adjacent beads (30, 150, 300) is stronger with one adjacent bead (30, 150, 300) compared to the other adjacent bead (30, 150, 300). Additionally, it may be advantageous to magnetize link (40) such that link (40) may encourage magnets (60, 100, 160, 200, 240) to float to a predetermined side of a magnetic chamber, thereby controlling which adjacent bead (30, 150, 300) has a stronger magnetic field compared to the other adjacent bead (30, 150, 300). In other instances, it may be desirable to use a magnet (60, 100) of different magnetic strength in various beads (30, 150, 300) in order to control and vary the magnetic fields generated by device (20).

Figure 23:
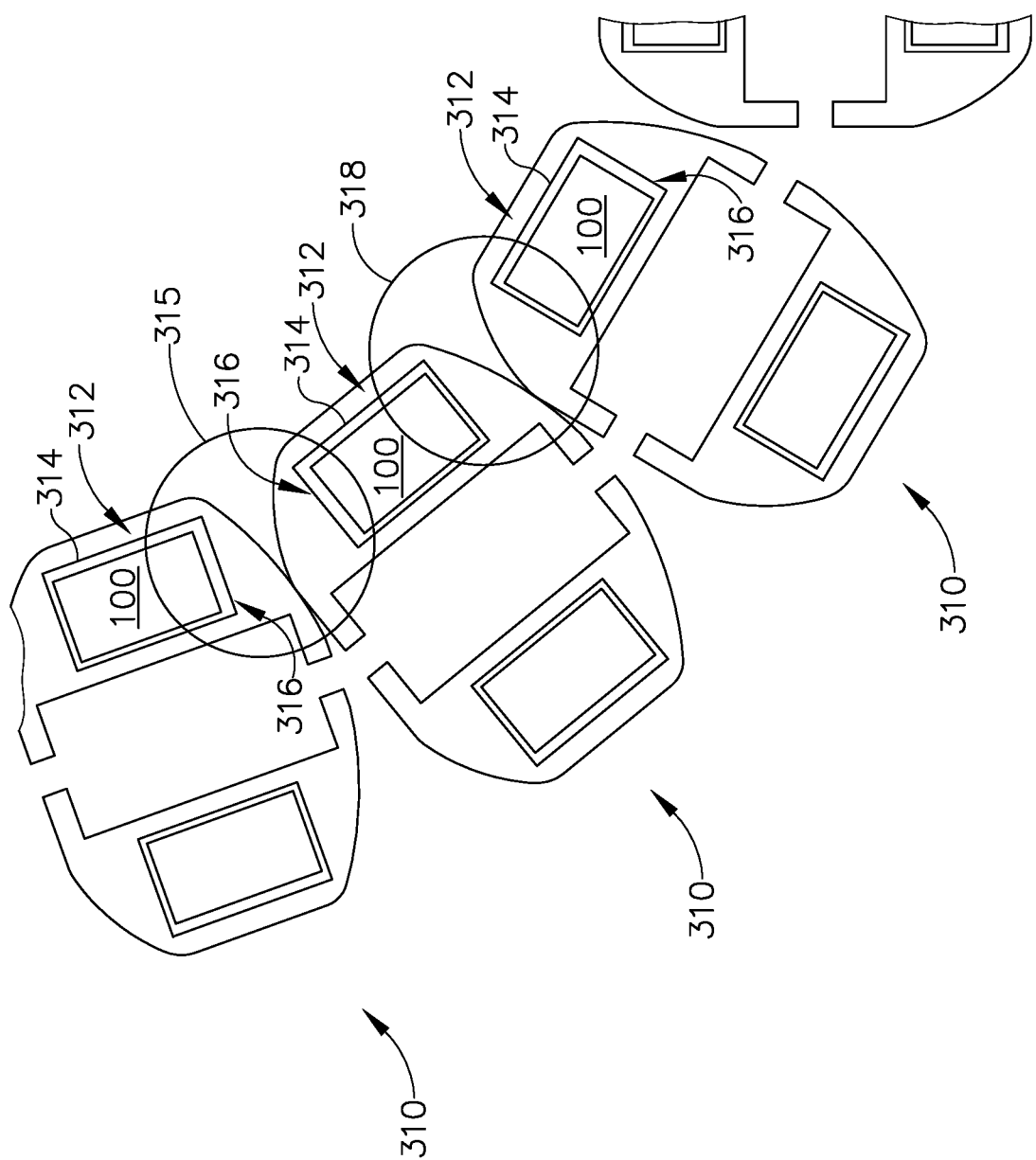
FIG. 23 depicts a top cross-sectional view of alternative beads housing magnets of FIG. 6 that may be readily incorporated into the sphincter augmentation device of FIG. 3.

FIG. 23 shows a plurality of alternative beads (310), where each bead (310) houses one magnet (100), that may be readily incorporated into device (20) described above. While one magnet (100) is housed within each bead (310), it should be understood a plurality of magnets (100) may be "stacked" together and housed within a single bead (310). Any suitable number of magnets (100) used in a single bead (310) will be apparent to one having ordinary skill in the art in view of the teachings herein. Beads (310) may be substantially similar to beads (30, 150, 300) described above, with differences elaborated below. Therefore, adjacent beads (310) may be connected by links (40) such that beads (310) may expand and contract between a contracted configuration and an expanded configuration while magnets (100) magnetically bias the plurality of beads (310) toward the contracted configuration.

Each bead (310) defines a magnetic chamber (312) dimensioned to slidably house magnet (100) such that magnet (100) may translate, slide, or otherwise "float" toward and away adjacent beads (310). Because magnet (100) may translate toward and away from adjacent beads (310), a magnetic field (318) generated by adjacent beads (310) is stronger than a magnetic field (315) generated by the opposite adjacent bead (310). In particular, magnetic chamber (312) extends along a chamber length (314) that spans toward adjacent beads (310). Chamber length (314) is longer than the length of magnet (100). Magnetic chamber (312) is further dimensioned to slidably house magnet (100) such that magnet (100) may translate along a path defined by chamber length (314).

Since magnet (100) is slidably housed within magnetic chamber (312), magnet (100) may slide closer to one adjacent bead (310), thereby defining a gap (316) within magnetic chamber (312). Magnetic field (315) generated by the sides of adjacent magnets (100) defining gap (316) is weaker than magnetic field (318) generated by sides of adjacent magnets (100) not defining gap (316). This is due in part to the fact the portions of adjacent magnets (100) generating the stronger magnetic field (318) are closed to each other than the portions of adjacent magnets (100) generating the weaker magnetic field (315). Magnets (100) may slide within magnetic chamber (312) along the path defined by chamber length (314) to different positions within magnetic chamber (312) as beads (310) transition between the contracted state and the expanded state such that the strength of magnetic fields (318, 315) compared to each other may change as beads (310) expand and contract. In other examples, magnets (100) may be fixed within beads (310), but offset along the path defined by chamber length (314) such that one magnetic field (318) is always stronger than the other magnetic field (315).

Figure 24:
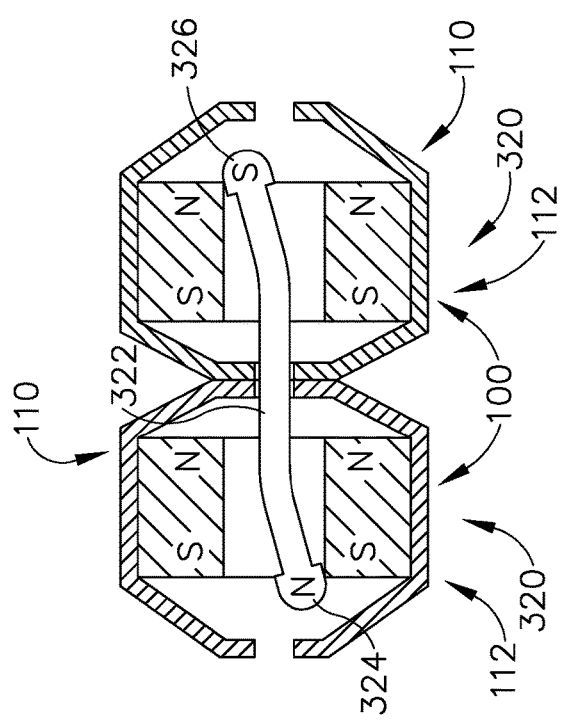
FIG. 24 depicts a top cross-sectional view of alternative beads housing magnets of FIG. 6, and an alternative link, both of which may be readily incorporated into the sphincter augmentation device of FIG. 3, where the beads are in a contracted configuration.
Figure 25:
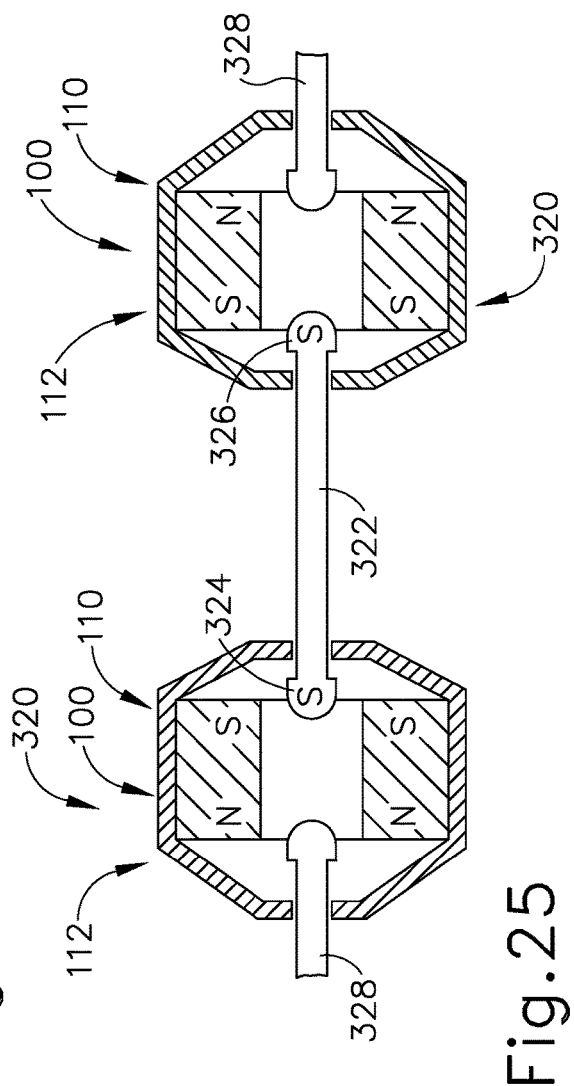
FIG. 25 depicts a top cross-sectional view of the beads and link of FIG. 24, where the beads are in an expanded configuration.

In some instances where magnet (100) is slidably housed within magnetic chamber (312), it may be desirable to encourage magnet (100) to translate to a predetermined side of magnetic chamber (312), thereby controlling which adjacent bead (310) has the stronger magnetic field (318) and which adjacent bead (310) has the weaker field (315). FIGS. 24-25 show an exemplary pair of beads (320) coupled by a magnetic link (322) that may be readily incorporated into device (20) described above. Beads (320) are substantially similar to beads (310) described above. Therefore, beads (320) house magnets (100) such that magnets (100) may slide within beads (320) toward and away from adjacent beads (320). Magnetic link (322) is slidably attached to adjacent beads (320) such that adjacent beads (320) may transition between the contracted state (as shown in FIG. 24) and the expanded state (as shown in FIG. 25). Magnetic link (322) includes a north pole section (324) terminating into a ball tip and a south pole section (326) terminating into a ball tip. Ball tip of north pole section (324) is slidably contained within the first magnetic bead (320) while ball tip of south pole section (326) is slidably contained within second magnetic bead (320).

As best seen in FIG. 24, when beads (320) are in the contracted state, ball tip of north pole section (324) is adjacent to south pole section (112) of magnet (100) within the first bead (320) (on the left); while ball tip of south pole section (326) is adjacent to north pole section (110) of magnet (100) within second bead (320) (on the right). Therefore, the magnetic attraction between ball tip of north pole section (324) and south pole section (112) of the magnet (100) within first bead (320) (on the left) may pull magnet (100) within first bead (320) toward second bead (320) (on the right). Similarly, the magnetic attraction between ball tip of south pole section (326) and north pole section (110) of magnet (100) within second bead (320) (on the right) may pull magnet (100) within second bead (320) toward first bead (320) (on the left). As such, magnetized link (322) may help encourage magnets (100) within adjacent beads (320) to translate toward each other in the contracted position. Of course, magnetized link (322) may be attached to beads (320) in the reversed order such that magnetized link (322)

may help encourage magnets (100) within adjacent beads (320) to translate away from each other in the contracted position.

As best seen in FIG. 25 when beads (320) are in the expanded state, ball tip of north pole section (324) is adjacent to north pole section (110) of magnet (100) within the first bead (320) (on the left); while ball tip of south pole section (326) is adjacent to south pole section (112) of magnet (100) within second bead (320) (one the right). Therefore, the magnetic repulsion between ball tip of north pole section (324) and north pole section (110) of the magnet (100) within first bead (320) (on the left) may push magnet (100) within first bead (320) away from second bead (320) (on the right). Similarly, the magnetic repulsion between ball tip of south pole section (326) and south pole section (112) of magnet (100) within second bead (320) (on the right) may pull magnet (100) within second bead (320) away from first bead (320) (on the left). As such, magnetized link (322) may help encourage magnets (100) within adjacent beads (320) to translate away from one other in the contracted position. Of course, magnetized link (322) may be attached to beads (320) in the reversed order such that magnetized link (322) may help encourage magnets (100) within adjacent beads (320) to translate toward each other in the expanded position.

In the current examples, each bead (320) contains a magnetized link (322) and a non-magnetized link (328) such that links (322, 328) extend around device (20) in an alternating fashion, however this is merely optional. Any suitable arrangement of magnetized links (322) and non-magnetized links (328) may be used as would be apparent to one having ordinary skill in the art in view of the teachings herein. In some instances, only magnetized links (322) may be used. In some instances, a variety of magnetized links (322) may be used having different magnetic strengths. As would be apparent to one having ordinary skill in the art in view of the teachings herein, any suitable arrangement of magnetized links (322) and non-magnetized links (328) may be used to encourage a desired shape of device (20) in the contracted state, in the expanded state, or any position in-between.

Figure 28:
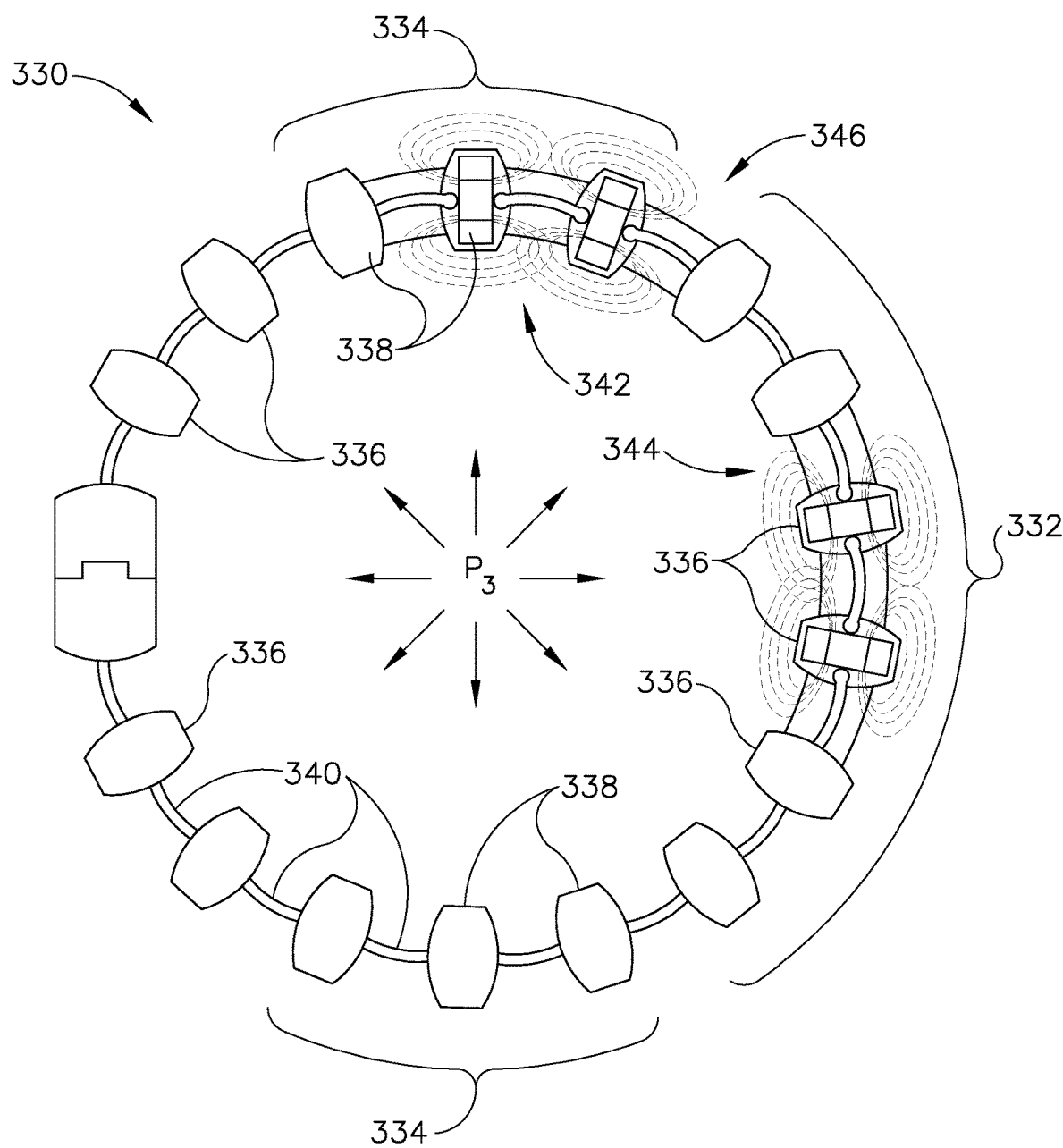
FIG. 28 depicts a top plan view of the sphincter augmentation device of FIG. 26, in a fully expanded configuration, with selected portions cut away for further clarity.

FIGS. 26-28 show an alternative sphincter augmentation device (330) that may be used in replacement of device (20) described above. Device (330) is substantially similar to device (20) described above, with differences elaborated below. Device (330) includes magnetic beads (336, 338), which may be substantially similar to beads (30) and corresponding magnetics (60) described above. Therefore, adjacent beads (336, 338) of device (330) are slidable connected by links (340). Links (340) may be substantially similar to links (40, 322, 328) described above. Beads (336, 338) may expand and contract relative to each other between a contracted state and an expanded state in similar fashion to device (20) described above while being magnetically biased to the contracted state, with differences described below.

In particular, device (330) includes two clusters of stronger magnetic beads (332) and two clusters of weaker magnetic beads (334). Clusters of magnetic beads (332, 334) are arranged to generate magnetic fields (342, 344, 346) of varying strengths such that device (330) forms an elongated oval shape in the contracted state (as shown in FIG. 26). While clusters of magnetic beads (332, 334) are arranged to form an oval shape in the current example, this is merely exemplary, as clusters of magnetic beads (332, 334) may be arranged to generate magnetic field (342, 344, 346) of varying strengths to form any suitable shape as would be apparent to one having ordinary skill in the art in view of the teachings herein.

Clusters of stronger magnetic beads (332) include an array of individual strong magnetic beads (336) coupled by links (340); while clusters of weaker magnetic beads (334) include an array of individual weaker magnetic beads (338) coupled by links (340). Stronger magnetic beads (336) include magnets with a strong magnetic flux; while weaker magnetic beads (338) include magnets with a relatively weaker magnetic flux. Therefore, magnetic fields (342) generated between adjacent weaker magnetic beads (338) are weaker relative to magnetic fields (344) generated between adjacent stronger magnetic beads (336). Additionally, magnetic fields (346) generated between stronger magnetic beads (336) and adjacent weaker magnetic beads (338) will be valued somewhere between strong magnetic field (346) and weaker magnetic field (344).

FIG. 26 shows device (330) in a contracted state under a first radially outward pressure (P1) imparted on device (330) from expansion of LES (6). For exemplary purposes only, first radially outward pressure (P1) may be between 0.00 mm/Hg and 25 mm/Hg. As shown in FIG. 27, since weak magnetic beads (338) are attracted to each other via a weak magnetic field (342) as compared to stronger magnetic field (344) and intermediary magnetic field (346), weak magnetic beads (338) may begin to expand relative to each other under a second radial outward force (P2) from expansion LES (6), prior to stronger magnetic beads (336) expanding relative to each other. For exemplary purposes only, second radially outward pressure (P2) may be around values beginning to exceed 35 mm/Hg. Therefore, under second radial outward force (P2), device (330) may expand to an intermediary expanded state, as shown in FIG. 27. FIG. 28 shows device (330) in a fully expanded state where weak magnetic beads (338) and strong magnetic beads (336) are expanded relative to each other under a third radially outward force (P3) from expansion of LES (6). For exemplary purposes only, third radially outward force (P3) may be around 80 mm/Hg. Therefore, device (330) may maintain an elongated oval shape over a first range of radially outward pressures provided by expansion of LES (6), then device (330) may expand into a second, circular, shape in response to a larger radially outward pressure provided by expansion of LES (6). Allowing different shapes of device (330) in the contracted and partially expanded shape may allow for device (330) to better encompass the targeted sphincter, such as LES (6), an anal sphincter, or any other suitable sphincter as would be apparent to one having ordinary skill in the art in view of the teachings herein.

In some instances, it may be desirable to use different thickness of magnets in magnetic beads (336, 338). This may enable the tuning of both the overall diameter of device (330) in smaller selectable increments, as well as the ability to tube the magnetic field strength by control the distance and mass of the magnet in a more incremental manner, thereby lowering the overall compressive force for the same size of bead geometry.

When device (330) increases in perimeter, a mixture of magnet sizes within beads (336, 338) could be swapped out in order to create larger magnetic attraction for the larger device (330), since the beads (336, 338) are capable of being farther apart in the fully expanded state than beads (336, 338) in the smaller diameter implant could be.

C. Magnetic Features to Promote Angular Alignment Between Adjacent Beads

As mentioned above adjacent beads (30, 150, 300, 310, 320, 336, 338) may be magnetically biased toward each other such that device (20, 330) is biased toward the contracted state (as shown in FIGS. 3, 5B, and 26). In particular, the magnetic bias of adjacent beads (30, 150, 300, 310, 320, 336, 338) is due, at least in part, to the north-south pole alignment of magnets (60, 100, 160, 200, 240) in adjacent beads (30, 150, 300, 310, 320, 336, 338). However, as exemplified in magnet (100), since north pole sections (110) and south pole sections (112) of magnet (100) cover the entirety of annular axially presented surfaces (102, 104), adjacent beads (30, 150, 300, 310, 320, 336, 338) may be magnetically attracted to each other, regardless of the rotational position of bead (30, 150, 300, 310, 320, 336, 338) about link (40, 322, 328, 340) relative to an adjacent bead (30, 150, 300, 310, 320, 336, 338). This may cause difficulties to suitably align beads (30, 150, 300, 310, 320, 336, 338) during assembly or to maintain alignment during exemplary use.

In some instances, bead (30, 150, 300, 310, 320, 336, 338) may have a resting contact surface configured to abut against the resting contact surface of a directly adjacent bead (30, 150, 300, 310, 320, 336, 338). If bead (30, 150, 300, 310, 320, 336, 338) is rotated about link (40, 322, 328, 340) relative to adjacent beads (30, 150, 300, 310, 320, 336, 338) such that resting contact surfaces are not suitably aligned, resting contact surfaces may not make contact with each other when device (20, 330) is in the contracted state, which may cause undesirable consequences. Therefore, it may be desirable to magnetically "tune" device (20, 330) to ensure that adjacent beads (30, 150, 300, 310, 320, 336, 338) are magnetically biased to the contracted state and are also magnetically biased to be rotationally aligned with each other about link (40, 322, 328, 340) (i.e. "clocked").

Figure 29:
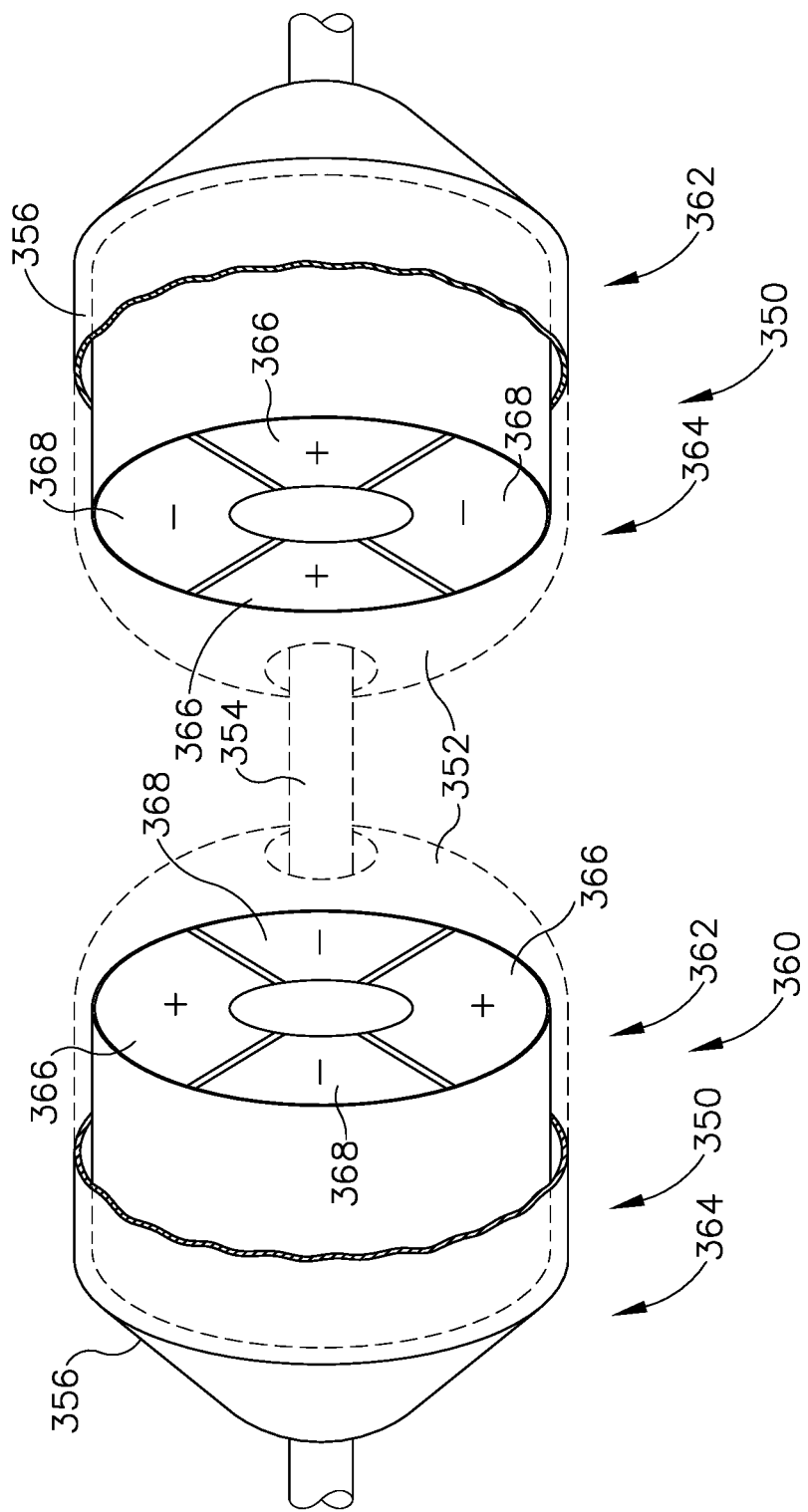
FIG. 29 depicts a perspective view of an alternative pair of beads and magnet assemblies that may be readily incorporated into the device of FIG. 3 or 26, with selected portions cut away for further clarity.

FIG. 29 shows alternative beads (350), link (354), and magnet assemblies (360) that may be readily incorporated into device (20, 330) described above. Beads (350) may be substantially similar to bead (30, 150, 300, 310, 320, 336, 338) described above, with differences elaborated below. Beads (350) include a housing assembly (356) that houses a respective magnet assembly (360) and a portion of associated links (354). Therefore, adjacent beads (350) may be connected by links (354) such that beads (350) may expand and contract between a contracted configuration and an expanded configuration while respective magnet assemblies (360) magnetically bias the plurality of beads (350) toward the contracted configuration. Beads (350) include resting contact surfaces (352) configured to abut against each other in the contracted configuration. As will be described in greater detail below, magnet assemblies (360) are configured to generate magnetic fields with adjacent magnet assemblies (360) to magnetically bias corresponding beads (350) to a predetermined, "clocked," rotational position about link (354) relative to each other.

Magnetic assemblies (360) extend between a first annular axially presented surface (362) and a second annular axially presented surface (364). Unlike magnet (100) described above, axially presented surfaces (362, 364) are not uniformly north pole sections and south pole sections. Instead, magnetic assemblies (360) include axially extending north pole sectors (366) and axially extending south pole sectors (368) that span between first annular axially presented surface (362) and second annular axially presented surface (364). Each individual north pole sector (366) associates with a corresponding individual south pole sector (368). In the current example, there are two north pole sectors (366) and two south pole sectors (368), where each sector spans about a quarter of each axially presented surface (362, 364). Also in the current example, sectors (366, 368) are arranged annularly in an alternating fashion such that each north pole sector (366) in an individual magnetic assembly (360) is adjacent to a south pole sector (368) within the same individual magnetic assembly (360). As will be described in greater detail below, any suitable number of sectors (366, 368) may be used in any suitable annular arrangement as would be apparent to one having ordinary skill in the art.

Individual north pole sectors (366) and individual south pole sectors (368) may be attached to each other/magnetized through any suitable means as would be apparent to one having ordinary skill in the art in view of teachings herein. When assembled, magnetic assemblies (360) are rotationally retained within respective housing assembly (356) such that magnetic assemblies (360) may not rotate relative to housing assembly (356) about an axis extending between annular axially presented surfaces (362, 364).

Magnetic assemblies (360) within adjacent beads (350) are polar mirrors of each other. In other word, magnetic assemblies (360) are positioned within beads (350) such that when assembled, a north pole sector (366) within a first bead (350) is adjacent to a south pole sector (368) of a second, adjacent bead (350). This alignment promotes a magnetic bias of beads (350) toward the contracted configuration in accordance with the description above. Additionally, with north pole sectors (366) and south pole sectors (368) extending between both annular axially presented surfaces (362, 364), north pole sectors (366) of a first bead (350) may be magnetically repelled by north pole sectors (366) of a second bead (350) when beads (350) are in the contacted configuration. Due to the mirrored polarity of adjacent magnetic assemblies (360), along with the axially extending north and south polar sectors (366, 368), this magnetic repulsion helps encourage angular alignment (i.e. clocking) between adjacent beads (350) about link (354) relative to each other. Therefore, magnetic assemblies may help adjacent beads (350) form angular alignment during assembly or maintain angular alignment during exemplary use.

Figure 30:
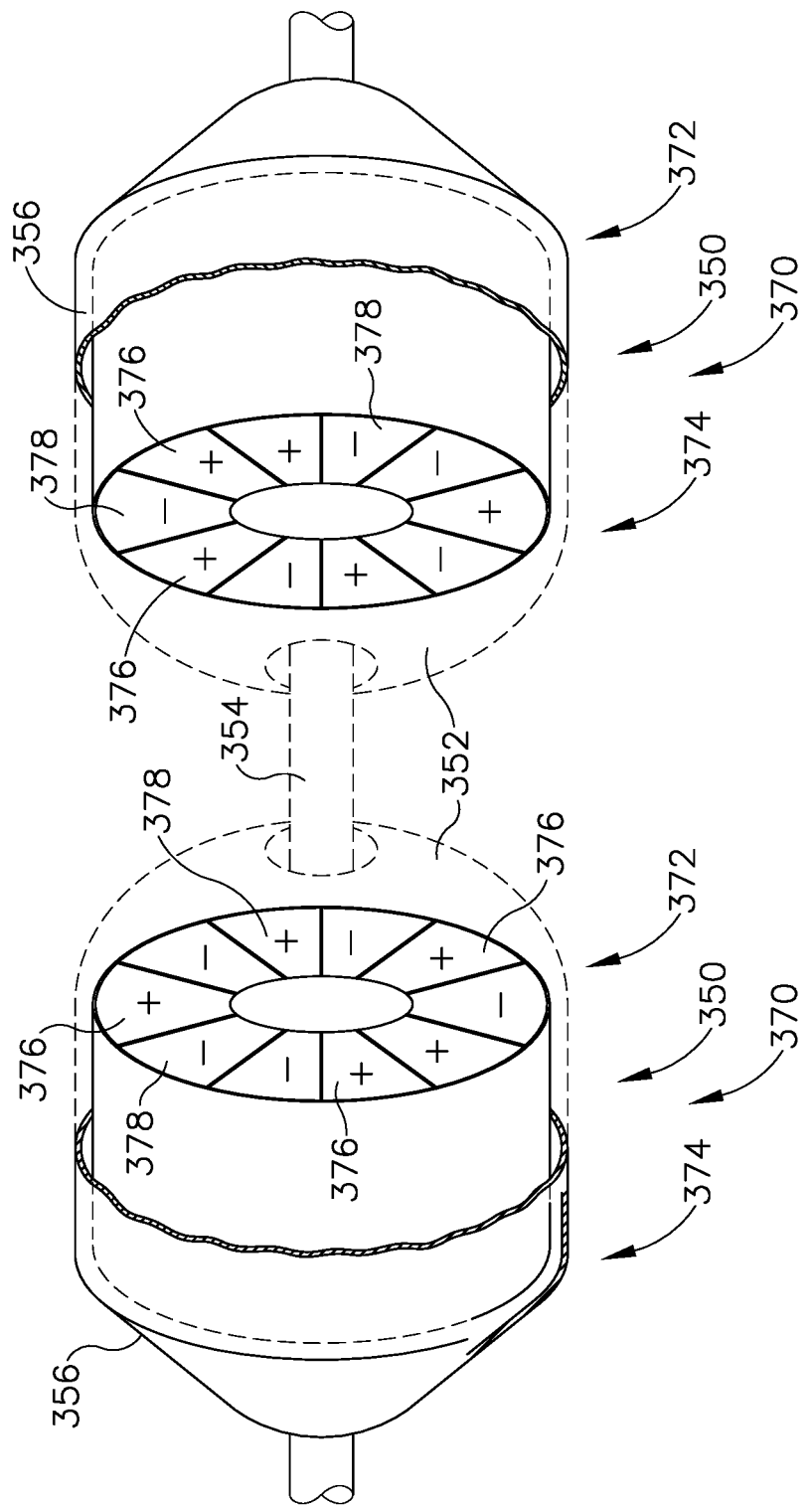
FIG. 30 depicts a perspective view of the pair of beads of FIG. 29 with an alternative magnet assembly, with selected portions cut away for further clarity.

FIG. 30 shows beads (350) and link (354) with alternative magnet assemblies (370) incorporated therein. Therefore, adjacent beads (350) may be connected by links (354) such that beads (350) may expand and contract between a contracted configuration and an expanded configuration while respective magnet assemblies (370) magnetically bias the plurality of beads (350) toward the contracted configuration. As will be described in greater detail below, magnet assemblies (370) are configured to generate magnetic fields with adjacent magnet assemblies (370) to magnetically bias corresponding beads (350) to a predetermined, "clocked," rotational position about link (354) relative to each other.

Magnetic assemblies (370) extend between a first annular axially presented surface (372) and a second annular axially presented surface (374). Unlike magnet (100) described above, axially presented surfaces (372, 374) are not uniformly north pole sections and south pole sections. Instead, magnetic assemblies (370) include axially extending north pole sectors (376) and axially extending south pole sectors (378) that span between first annular axially presented surface (372) and second annular axially presented surface (374). Each individual north pole sector (376) associates with a corresponding individual south pole sector (378). In the current example, there are five north pole sectors (376) and five south pole sectors (378), where each sector spans about a fifth of each axially presented surface (372, 374).

Also in the current example, sectors (376, 378) are arranged annularly in a fashion such that some north pole sectors (376) in an individual magnetic assembly (370) are adjacent only to south pole sector (378) within the same individual magnetic assembly (370); while some north pole sectors (376) in individual magnetic assembly (370) are adjacent to another north pole sector (376) and a south pole sector (378). Any suitable number of sectors (376, 378) may be used in any suitable annular arrangement as would be apparent to one having ordinary skill in the art.

Individual north pole sectors (376) and individual south pole sectors (378) may be attached to each other/magnetized through any suitable means as would be apparent to one having ordinary skill in the art in view of teachings herein. When assembled, magnetic assemblies (370) are rotationally retained within respective housing assembly (356) such that magnetic assemblies (370) may not rotate relative to housing assembly (356) about an axis extending between annular axially presented surfaces (362, 364).

Magnetic assemblies (370) within adjacent beads (350) are polar mirrors of each other. In other word, magnetic assemblies (370) are positioned within beads (350) such that when assembled, a north pole sector (376) within a first bead (350) is adjacent to a south pole sector (378) of a second, adjacent bead (350). This alignment promotes a magnetic bias of beads (350) toward the contracted configuration in accordance with the description above. Additionally, with north pole sectors (376) and south pole sectors (378) extending between both annular axially presented surfaces (372, 374), north pole sectors (376) of a first bead (350) may be magnetically repelled by north pole sectors (376) of a second bead (350) when beads (350) are in the contacted configuration. Due to the mirrored polarity of adjacent magnetic assemblies (370), along with the axially extending north and south polar sectors (376, 378), this magnetic repulsion helps encourage angular alignment (i.e. clocking) between adjacent beads (350) about link (354) relative to each other. Therefore, magnetic assemblies may help adjacent beads (350) form angular alignment during assembly or maintain angular alignment during exemplary use.

Figure 31:
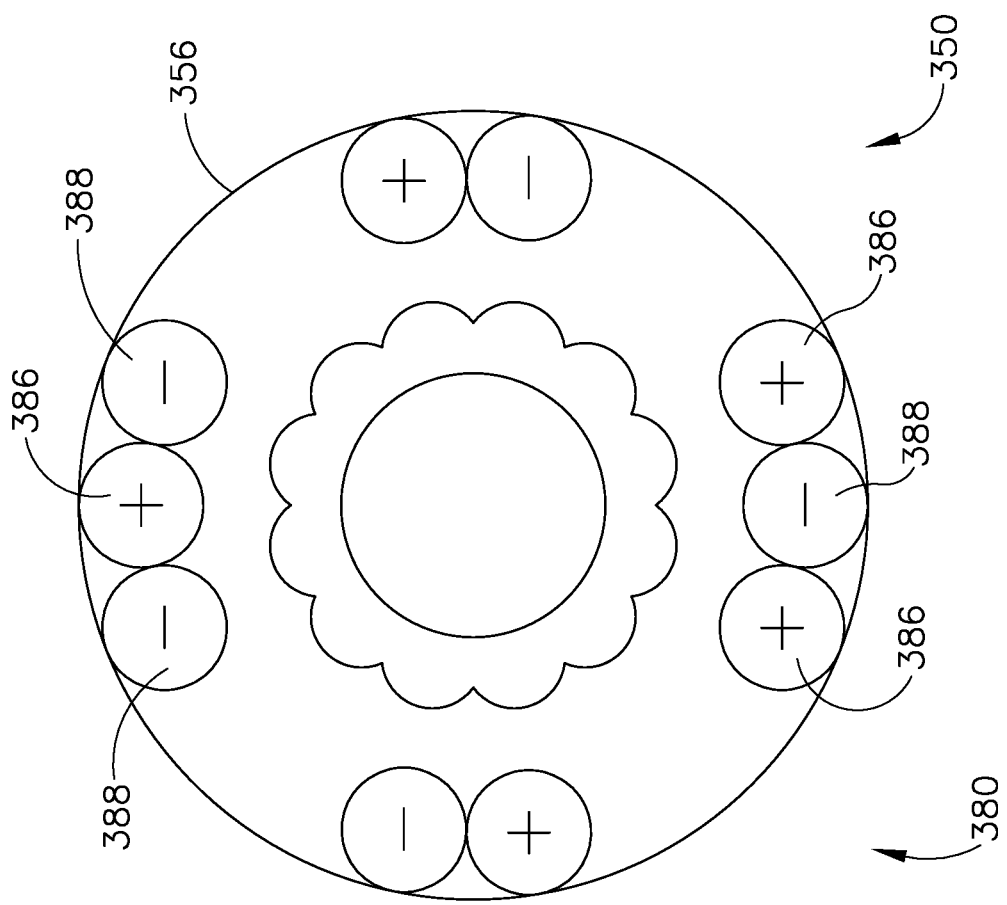
FIG. 31 depicts a front cross-sectional view of bead of FIG. 29 with an alternative magnet assembly.

While in the current examples, magnetic assemblies (360, 370) include north pole sectors (366, 376) and south pole sectors (368, 378), any suitable geometry may be used as would be apparent to one having ordinary skill in the art in view of the teachings herein. For example, FIG. 31 show an alternative magnetic assembly (380) including axially extending north pole rods (386) with corresponding axially extending south pole rods (388). Magnetic assembly (380) may be substantially similar to magnetic assembly (360, 370) described above, except the shape of north and south pole components are rods. While rods (386, 388) are used as an alternative example, any other suitable geometry may be incorporated as would be apparent to one having ordinary skill in the art in view of the teachings herein.

Figure 33:
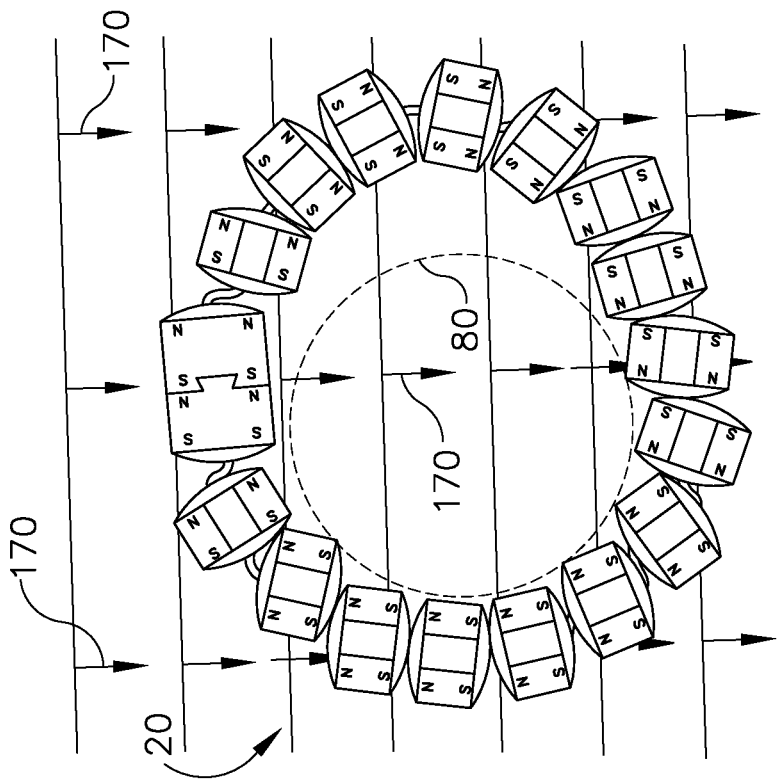
FIG. 33 depicts a top plan view of the device of FIG. 3, where the device is exposed to an MRI uniform field.
Figure 32:
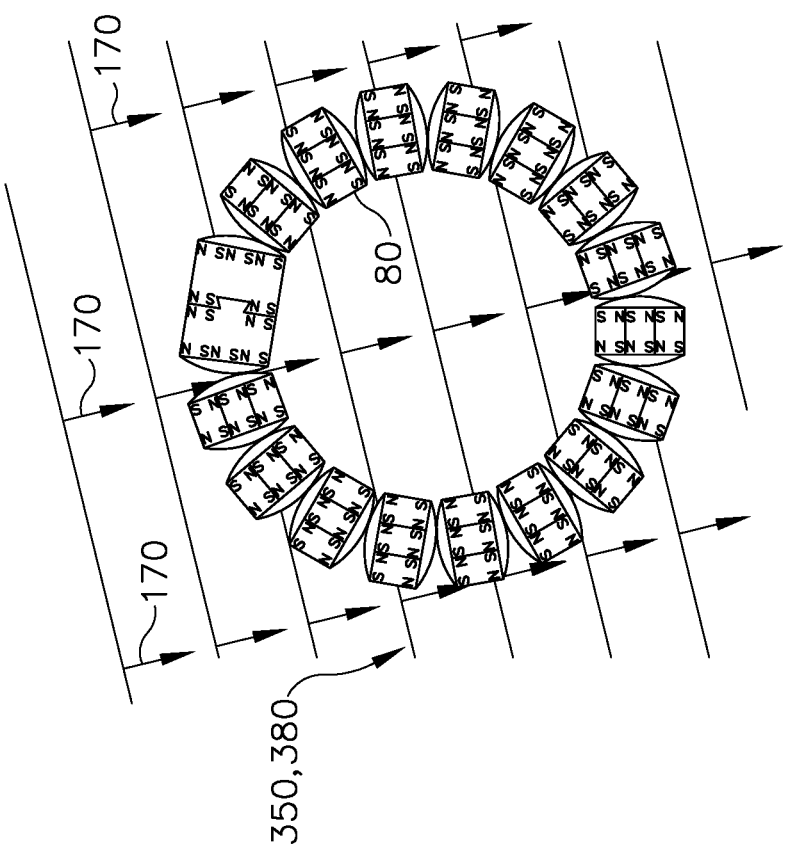
FIG. 32 depicts a top plan view of a device the includes a plurality of beads as shown in FIG. 31, where the device is exposed to an MRI uniform field.

In addition to providing advantages by rotationally clocking beads (350), magnetic assemblies (360, 370, 380) having numerous north and south poles on each side of the magnetic assembly may provide advantages when exposed to an external magnetic field. For example, as shown in FIG. 32, when a device (20) composed of beads (350) with magnetic assemblies (380) is exposed to a uniform MRI field (170). Magnetic assemblies (380) ability to resist twisting relative to each other due to the arrangement of north pole rods (386) and south pole rods (388). Therefore, magnetic assemblies (380) may prevent uniform MRI field (170) from overtly distorting the target contracted state shape (80) of beads (350), as compared to if device (20) is exposed to uniform MRI field (170), as shown in FIG. 33.

D. Tissue Compression Limits to Minimize Inadvertent Tissue Damage while Maintaining Sphincter Control It may be desirable to have device (20, 330) or any variation of device (20, 330) described herein has operational compression limits which device (20, 330) may impart onto tissue creating a sphincter, such as LES (6). It may be desirable to have compression limits between a pressure range having a lower limit such that device (20, 330) may function as a sphincter reinforcement device, but with an upper limit where device (20, 330) does not damage tissue. For esophageal reinforcement, this pressure range may be above the gastric pressure, subtracting what the sphincter can still exert, but less than the pressure that induces discomfort or inhibits swallowing. A rectal sphincter will have similar requirements with different pressures for significantly different reasons. Some ways to control these compression limits is for beads (30) to have predefined contacts in the contracts state to limit long term tissue compression under a predefined threshold. Another way is to have increased internal diameter surface area contact between device (20) and the tissue being restricted.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An implantable restriction device, the implantable restriction device comprising: (a) a plurality of beads, wherein each bead comprises: (i) a housing comprising a contact surface, (ii) a passageway extending through the housing, wherein the passageway defines an axis, and (iii) at least one magnet disposed around the passageway; and (b) a plurality of links joining the beads together, wherein portions of the links are slidably disposed in corresponding passageways of the beads such that the plurality of beads are operable to transition between an constricted configuration and an expanded configuration, wherein contact surfaces of adjacent beads in the plurality of beads are configured to abut against each other in the constricted configuration, wherein the at least one magnet of adjacent beads in the plurality of beads generate an interactive magnetic field focused on the abutting contact surfaces of adjacent beads in the plurality of beads.

Example 2

The implantable restriction device of Example 1, wherein the at least on magnet comprises at least one annular magnet.

Example 3

The implantable restriction device of Example 2, wherein the at least one annular magnet in at least one bead of the plurality of beads comprises a chamfered corner.

Example 4

The implantable restriction device of Example 3, wherein the at least one annular magnet comprises an outer diameter, wherein the chamfered corner is located on the outer diameter.

Example 5

The implantable restriction device of any one or more of Examples 2 through 4, wherein the at least one annular magnet in at least one bead of the plurality of beads comprises a radiused corner.

Example 6

The implantable restriction device of Example 5, wherein the at least one annular magnet comprises an inner diameter, wherein the radiused corner is located on the inner diameter.

Example 7

The implantable restriction device of any one or more of Examples 1 through 6, wherein the contact surface comprises a flat surface.

Example 8

The implantable restriction device of Example 7, wherein the flat surface extends along a plane that intersects with a center point of the implantable restriction device.

Example 9

The implantable restriction device of any one or more of Examples 1 through 8, wherein the housing defines a magnet chamber configured to house the at least one magnet.

Example 10

The implantable restriction device of Example 9, where the at least one magnet extends along a first length, wherein the magnet chamber extends along a second length.

Example 11

The implantable restriction device of any one or more of Examples 9 through 10, wherein the second length is longer than the first length such that the at least one magnet is configured to translate within the magnet chamber.

Example 12

The implantable restriction device of Example 11, wherein at least one link in the plurality of links in magnetized.

Example 13

The implantable restriction device of Example 12, wherein the at least one link is configured to pull the at least one magnet of adjacent beads toward each other in the contracted configuration.

Example 14

The implantable restriction device of any one or more of Examples 12 through 13, wherein the at least one link is configured to push the at least one magnet of adjacent beads away from each other in the contracted configuration.

Example 15

The implantable restriction device of any one or more of Examples 1 through 14, wherein the plurality of beads comprises a first group of beads and a second group of beads, wherein the at least one magnet in the first group of beads comprises a first magnetic flux density, wherein the at least one magnet in the second group of beads comprises a second magnetic flux density.

Example 16

The implantable restriction device of Example 15, wherein the first magnetic flux density is greater than the second magnetic flux density.

Example 17

An implantable restriction device, the implantable restriction device comprising:
(a) at least two beads, wherein each bead comprises: (i) a housing comprising a contact surface, (ii) a passageway extending through the housing, wherein the passageway defines an axis, and (iii) at least one magnet disposed around the passageway; and (b) at least one link joining the beads together, wherein portions of the links are slidably disposed in corresponding passageways of the beads such that the at least two beads are operable to transition between an constricted configuration and an expanded configuration, wherein contact surfaces of adjacent beads in the at least two beads are configured to abut against each other in the constricted configuration, wherein the at least one magnet of adjacent beads in the plurality of beads is configured to generate an interactive magnetic field extending along a field focused axis that intersects through abutting contact surfaces of adjacent beads in the at least two beads in the constricted configuration.

Example 18

An implantable restriction device, the implantable restriction device comprising: (a) a series of beads interconnected to form a ring, wherein the ring is configured to transition between a contracted configuration and an expanded configuration; and (b) at least one ring-shaped magnet contained within each bead in the series of beads, wherein the at least one ring-shaped magnet of a first bead in the series of beads is configured to generate a first magnetic field, wherein the at least one ring-shaped magnet of a second bead in the series of beads is configured to generate a second magnetic field, where the first bead and the second bead are adjacent to each other, wherein the first magnetic field and the second magnetic field are focused at substantially a predetermined contact point between the first bead and the second bead.

Example 19

The implantable restriction device of Example 18, wherein the first magnet field and the second magnetic field are most intense at the predetermined contact point.

Example 20

The implantable restriction device of any one or more of Examples 18 through 19, wherein the series of beads comprise a non-ferrous material.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implantable restriction device, the implantable restriction device comprising:
   (a) a plurality of beads, wherein each bead comprises:
      (i) a housing comprising a contact surface,
      (ii) a passageway extending through the housing, wherein the passageway defines an axis, and
      (iii) at least one magnet disposed around the passageway, wherein the at least one magnet comprises at least one annular magnet, wherein the at least one annular magnet in at least one bead of the plurality of beads comprises a chamfered corner and a radiused corner; and
   (b) a plurality of links joining the beads together, wherein portions of the links are slidably disposed in corresponding passageways of the beads such that the plurality of beads are operable to transition between an constricted configuration and an expanded configuration, wherein contact surfaces of adjacent beads in the plurality of beads are configured to abut against each other in the constricted configuration, wherein the at least one magnet of adjacent beads in the plurality of beads generate an interactive magnetic field focused on the abutting contact surfaces of adjacent beads in the plurality of beads.

2. The implantable restriction device of claim 1, wherein the at least one annular magnet comprises an outer diameter, wherein the chamfered corner is located on the outer diameter.

3. The implantable restriction device of claim 1, wherein the at least one annular magnet comprises an inner diameter, wherein the radiused corner is located on the inner diameter.

4. The implantable restriction device of claim 1, wherein the contact surface comprises a flat surface.

5. The implantable restriction device of claim 1, wherein the housing defines a magnet chamber configured to house the at least one magnet.

6. The implantable restriction device of claim 5, wherein the at least one magnet extends along a first length, wherein the magnet chamber extends along a second length.

7. The implantable restriction device of claim 6, wherein the second length is longer than the first length such that the at least one magnet is configured to translate within the magnet chamber.

8. The implantable restriction device of claim 1, wherein at least one link in the plurality of links in magnetized.

9. The implantable restriction device of claim 8, wherein the at least one link is configured to pull the at least one magnet of adjacent beads toward each other in the contracted configuration.

10. The implantable restriction device of claim 8, wherein the at least one link is configured to push the at least one magnet of adjacent beads away from each other in the contracted configuration.

11. The implantable restriction device of claim 1, wherein the plurality of beads comprises a first group of beads and a second group of beads, wherein the at least one magnet in the first group of beads comprises a first magnetic flux density, wherein the at least one magnet in the second group of beads comprises a second magnetic flux density.

12. The implantable restriction device of claim 11, wherein the first magnetic flux density is greater than the second magnetic flux density.

13. An implantable restriction device, the implantable restriction device comprising:
   (a) at least two beads, wherein each bead comprises:
      (i) a housing comprising a contact surface,
      (ii) a passageway extending through the housing, wherein the passageway defines an axis, and
      (iii) at least one magnet disposed around the passageway; and
   (b) a plurality of links joining the beads together, wherein at least one of the links is magnetized, wherein portions of the links are slidably disposed in corresponding passageways of the beads such that the at least two beads are operable to transition between an constricted configuration and an expanded configuration, wherein contact surfaces of adjacent beads in the at least two beads are configured to abut against each other in the constricted configuration, wherein the at least one magnet of adjacent beads in the plurality of beads is configured to generate an interactive magnetic field extending along a field focused axis that intersects through abutting contact surfaces of adjacent beads in the at least two beads in the constricted configuration.

14. An implantable restriction device, the implantable restriction device comprising:
(a) a plurality of beads, wherein each bead comprises:
  (i) a housing comprising a contact surface, wherein the housing defines a magnet chamber configured to house the at least one magnet,
  (ii) a passageway extending through the housing, wherein the passageway defines an axis, and
  (iii) at least one magnet disposed around the passageway, wherein the at least one magnet extends along a first length, wherein the magnet chamber extends along a second length, wherein the second length is longer than the first length and the magnet is slidably disposed within the magnet chamber such that the at least one magnet is slidable along the second length within the magnet chamber, toward an adjacent bead of the plurality of beads; and
(b) a plurality of links joining the beads together, wherein portions of the links are slidably disposed in corresponding passageways of the beads such that the plurality of beads are operable to transition between an constricted configuration and an expanded configuration, wherein contact surfaces of adjacent beads in the plurality of beads are configured to abut against each other in the constricted configuration, wherein the at least one magnet of adjacent beads in the plurality of beads generate an interactive magnetic field focused on the abutting contact surfaces of adjacent beads in the plurality of beads.

* * * * *